(12) United States Patent
Zheng et al.

(10) Patent No.: US 8,602,994 B2
(45) Date of Patent: Dec. 10, 2013

(54) METHOD FOR ULTRASOUND VIBROMETRY USING ORTHOGONAL BASIS FUNCTIONS

(75) Inventors: Yi Zheng, Cold Spring, MN (US);
Aiping Yao, St. Cloud, MN (US); James F. Greenleaf, Rochester, MN (US);
Shigao Chen, Rochester, MN (US);
Matthew W. Urban, Rochester, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/254,227

(22) PCT Filed: Mar. 9, 2010

(86) PCT No.: PCT/US2010/026676
§ 371 (c)(1),
(2), (4) Date: Sep. 1, 2011

(87) PCT Pub. No.: WO2010/104863
PCT Pub. Date: Sep. 16, 2010

(65) Prior Publication Data
US 2011/0319756 A1     Dec. 29, 2011

Related U.S. Application Data

(60) Provisional application No. 61/209,584, filed on Mar. 9, 2009.

(51) Int. Cl.
*A61B 8/00*       (2006.01)
*G01H 1/00*       (2006.01)

(52) U.S. Cl.
USPC ............................................. 600/438; 73/579

(58) Field of Classification Search
USPC .............. 600/437, 443; 702/19, 22; 382/260; 345/441, 501, 552; 73/574, 579, 587, 73/609
See application file for complete search history.

(56) References Cited

U.S. PATENT DOCUMENTS

| 6,424,749 B1 | 7/2002 | Zhu et al. |
| 2005/0119834 A1 | 6/2005 | Kita et al. |
| 2007/0038095 A1 | 2/2007 | Greenleaf et al. |

OTHER PUBLICATIONS

International Search Report and Written Opinion as mailed on May 7, 2010 for International Application No. PCT/US2010/026676.

*Primary Examiner* — Michael Rozanski
(74) *Attorney, Agent, or Firm* — Quarles & Brady LLP

(57) ABSTRACT

A method for measuring a mechanical property of a subject includes using an ultrasound transducer to apply ultrasonic vibration pulses to a location in a subject in order to induce shear waves at multiple prescribed orthogonal frequencies in the subject. The ultrasound transducer is directed by an excitation signal that is composed of multiple orthogonal basis functions, each having a given frequency component corresponding to the prescribed orthogonal frequencies. The power level of each orthogonal basis function is independently adjustable. The excitation signal can be sparsely sampled, or portions of the excitation signal can be removed in order to improve tissue vibration and to provide for the interleaving ultrasonic vibration and detection pulses. Ultrasonic detection pulses are applied to at least one motion detection point, from which echo signals are received. From the received echo signals, a motion signal is determined, from which mechanical properties of the subject are calculated.

15 Claims, 14 Drawing Sheets

METHOD FOR ULTRASOUND VIBROMETRY USING ORTHOGONAL BASIS FUNCTIONS

CROSS-REFERENCE TO RELATED APPLICATIONS

This application claims the benefit of U.S. Provisional Patent Application Ser. No. 61/209,584 filed on Mar. 9, 2009, and entitled "Orthogonal Frequency Ultrasound Vibrometry," and is a national phase of International Application No. PCT/US2010/026676 filed on Mar. 9, 2010, entitled "Method for Ultrasound Vibrometry Using Orthogonal Basis Functions," incorporated by reference herein.

STATEMENT REGARDING FEDERALLY SPONSORED RESEARCH

This invention was made with government support under EB002167 and EB002460 awarded by the National Institutes of Health. The government has certain rights in the invention.

BACKGROUND OF THE INVENTION

The field of the invention is coherent imaging using vibratory energy, such as ultrasound and, in particular, systems and methods for shearwave dispersion ultrasound vibrometry ("SDUV").

There are a number of modes in which ultrasound can be used to produce images of objects. For example, an ultrasound transmitter may be placed on one side of the object and sound transmitted through the object to an ultrasound receiver placed on the other side of the object. With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("reflection," "backscatter," or "echo" mode).

There are a number of well known backscatter methods for acquiring ultrasound data. In the so-called "A-mode" method, an ultrasound pulse is directed into the object by an ultrasound transducer and the amplitude of the reflected sound is recorded over a period of time. The amplitude of the echo signal is proportional to the scattering strength of the reflectors in the object and the time delay is proportional to the range of the reflectors from the transducer. In the so-called "B-mode" method, the transducer transmits a series of ultrasonic pulses as it is scanned across the object along a single axis of motion. The resulting echo signals are recorded as with the A-mode method and their amplitude is used to modulate the brightness of pixels on a display. The location of the transducer and the time delay of the received echo signals locates the pixels to be illuminated. With the B-mode method, enough data are acquired from which a two-dimensional image of the reflectors can be reconstructed. Rather than physically moving the transducer over the subject to perform a scan it is more common to employ an array of transducer elements and electronically move an ultrasonic beam over a region in the subject.

The ultrasound transducer typically has a number of piezoelectric elements arranged in an array and driven with separate voltages ("apodizing"). By controlling the time delay, or phase, and amplitude of the applied voltages, the ultrasonic waves produced by the piezoelectric elements ("transmission mode") combine to produce a net ultrasonic wave focused at a selected point. By controlling the time delay and amplitude of the applied voltages, this focal point can be moved in a plane to scan the subject.

The same principles apply when the transducer is employed to receive the reflected sound ("receiver mode"). That is, the voltages produced at the transducer elements in the array are summed together such that the net signal is indicative of the sound reflected from a single focal point in the subject. As with the transmission mode, this focused reception of the ultrasonic energy is achieved by imparting separate time delays, or phase shifts, and gains to the echo signal received by each transducer array element.

There are a number of electronic methods for performing a scan using a transducer having an array of separately operable elements. These methods include linear array systems and phased array systems.

A linear array system includes a transducer having a large number of elements disposed in a line. A small group of elements are energized to produce an ultrasonic beam that travels away from the transducer, perpendicular to its surface. The group of energized elements is translated along the length of the transducer during the scan to produce a corresponding series of beams that produce echo signals from a two-dimensional region in the subject. To focus each beam that is produced, the pulsing of the inner elements in each energized group is delayed with respect to the pulsing of the outer elements. The time delays determine the depth of focus which can be changed during scanning. The same delay factors are applied when receiving the echo signals to provide dynamic focusing during the receive mode.

A phased array system commonly employs so-called phased array sector scanning ("PASS"). Such a scan is comprised of a series of measurements in which all of the elements of a transducer array are used to transmit a steered ultrasonic beam. The system then switches to receive mode after a short time interval, and the reflected ultrasonic wave is received by all of the transducer elements. Typically, the transmission and reception are steered in the same direction, $\theta$, during each measurement to acquire data from a series of points along a scan line. The receiver is dynamically focused at a succession of ranges, R, along the scan line as the reflected ultrasonic waves are received. A series of measurements are made at successive steering angles, $\theta$, to scan a pie-shaped sector of the subject. The time required to conduct the entire scan is a function of the time required to make each measurement and the number of measurements required to cover the entire region of interest at the desired resolution and signal-to-noise ratio. For example, a total of 128 scan lines may be acquired over a sector spanning 90 degrees, with each scan line being steered in increments of 0.70 degrees.

The same scanning methods may be used to acquire a three-dimensional image of the subject. The transducer in such case is a two-dimensional array of elements which steer a beam throughout a volume of interest or linearly scan a plurality of adjacent two-dimensional slices.

Recently, an ultrasound technique for measuring mechanical properties of tissues called shearwave dispersion ultrasound vibrometry ("SDUV") was developed and described, for example, in co-pending U.S. patent application Ser. Nos. 10/956,461 and 11/536,330, which are herein incorporated by reference in their entirety. In SDUV, a focused ultrasound beam, operating within FDA safety limits, is applied to a subject to generate harmonic shear waves in a tissue of interest. The propagation speed of the induced shear wave is frequency dependent, or "dispersive," and relates to the mechanical properties of the tissue of interest. Shear wave speeds at a number of frequencies are measured by pulse echo ultrasound and subsequently fit with a theoretical dispersion model to inversely solve for tissue elasticity and viscosity. These shear wave speeds are estimated from the phase of tissue vibration that is detected between two or more points with known distance along the shear wave propagation path.

One feature of the SDUV method is the use of a so-called "binary pushing pulse" that allows the operation of one single array ultrasound transducer for both motion excitation and the echo signal detection. The transducer focuses ultrasound at one location, the "vibration origin," to vibrate the tissue of interest and then electronically steers its focus to another location, a "motion detection point," for echo signal vibration detection. Instead of continuously vibrating the tissue of interest, the "pushing" ultrasound is turned on during a vibration time period to vibrate the tissue and turned off to provide a time window for the pulse echo motion detection. When the pushing pulse is off, a series of short ultrasound pulses is transmitted to the motion detection location and a corresponding series of echo signals is received and processed to determine the tissue vibration. This intermittent pulse sequencing strategy allows both the production of a shear wave and the monitoring of its propagation at the same time with a single array transducer.

Tissue mechanical properties such as elastic modulus, or stiffness, and viscosity are often related to the pathological state of the tissue. Palpation, an ancient diagnostic tool, is still widely used by physicians today to examine patients by touch. However, the reliability and specificity of palpation varies based on physicians' experience, and is a subjective tool. Moreover, if abnormal tissue is located deep, with respect to the skin surface, its detection by palpation is often difficult or impossible. It has been recognized that tissue shear moduli have high dynamic ranges in biological tissues, and that these moduli significantly change during a pathological process.

Recently, noninvasive methods have been developed to quantitatively measure both tissue shear elasticity and viscosity, simultaneously, using so-called "ultrasound vibrometry" techniques. One such method uses ultrasound harmonic vibration and pulse-echo ultrasound detection, and is described by Y. Zheng, et al., in "Detection of Tissue Harmonic Motion Induced by Ultrasonic Radiation Force Using Pulse-Echo Ultrasound and Kalman Filter," *IEEE Trans. Ultrason. Ferroelectr. Freq. Control,* 2007; 54:290-300. This method uses the ultrasound radiation force to induce a shear wave in a tissue region with a single frequency at a time and uses the pulse-echo ultrasound to detect the shear wave propagation. This method requires repetitive measurements for several different harmonics. It also requires simultaneous vibration and detection that is problematic for practical implementations.

Another such method is SDUV, which is referred to above and additionally described, for example, by S. Chen, et al., in "Shearwave Dispersion Ultrasound Vibrometry (SDUV) for Measuring Tissue Elasticity and Viscosity," *IEEE Trans. Ultrason. Ferroelectr. Freq. Control,* 2009; 56:55-62. As noted, this method delivers focused ultrasound that generates an acoustic radiation force in a tissue region. The radiation force induces vibrations in the tissue, as well as a propagating shear wave. The vibration motion created in response to the shear wave propagation is detected using ultrasound-based pulse-echo measurement methods and appropriate signal processing techniques for motion detection. The motion amplitude and phase at a specified frequency are extracted using a signal processing technique such as Fourier analysis or fast Fourier transform, or a filter such as a Kalman filter, and used for shear wave speed estimation. The speed of the induced shear wave is measured by evaluating the phase shift of the shear wave at a given frequency over a propagation distance.

Measurements of shear wave speeds at multiple frequencies are then used to fit to a model to solve for the shear elasticity and viscosity, such as the Voigt model. The shear wave speed measurements can be fit with any viscoelastic model and are not restricted to the Voigt model.

The SDUV method has great potential to measure the viscoelastic material properties of stiffening liver tissue in fibrosis or cirrhosis, arterial stiffening due to atherosclerosis, myocardial stiffening due to dysfunction, and other applications.

The radiation force in SDUV is generated by an ultrasound transducer that transmits ultrasound waves in response to, for example, one of two kinds of signals. The first kind of signal produces an amplitude modulated ultrasound wave with a modulation frequency, $\omega_m$, and an ultrasound, or carrier, frequency, $\omega_c$. This type of ultrasound wave produces a force that has a dynamic component at $\omega_m$ and $2\cdot\omega_m$, when large carrier amplitude modulation is utilized, and at $2\cdot\omega_m$ when double sideband and suppressed carrier amplitude modulation is utilized. Using such method, a continuous vibration of the tissue is produced, and shear waves propagate outwards from the axis of the force, which can be detected at the same time. A typical range for the shear wave frequencies is 50-1000 Hz, while the ultrasound frequencies range from 1-10 MHz. In this case, two transducers are required, one for generating the radiation force with a single frequency component and another for the detection. The two transducers can be replaced by one transducer array, of which transducer elements are divided into two groups: one for vibration and another for detection. This process is repeated for several different vibration frequencies to evaluate the dispersion of the shear wave speed.

This method is not without its drawbacks. One exemplary drawback is that two transducers having two different center frequencies are required because the vibration and detection are operated at the same time. If the two transducers have similar center frequencies and bandwidth, there will be interference between the signals used for detection and vibration. Another exemplary drawback is that measurement time is prolonged because the responses of the vibration at several frequencies are measured separately.

The second kind of signal produces tone bursts of ultrasound energy. Using this second kind of signal, SDUV intermittently vibrates tissue and detects the vibration over a distance. In this case, a set of N tone bursts of length $T_b$ are repeated at a period of $T_p$, which corresponds to a rate, $f_p$, equal to $1/T_p$. This method could be thought of as amplitude modulation with a square wave with a duty cycle of $T_b \cdot f_p$. While the first SDUV approach produces a radiation force that has a single frequency component, the second approach produces a radiation force at the frequency, $f_p$, and its harmonics. For example, $f_p$ may be 100 Hz, and as a result, the shear wave harmonic components would be at 200 Hz, 300 Hz, 400 Hz, and so on. The harmonics in the shear wave spectrum should not be confused with so-called "harmonic imaging" common in medical ultrasound imaging, as, for example, the frequencies involved with harmonic imaging are in the megahertz range. The advantage of this tone burst method is that it allows the use of the same transducer array for both vibration and detection at different times. It also measures the tissue response of several harmonics at the same time.

Despite these benefits, this method is also not without its drawbacks. One exemplary drawback is that only a small percentage of received samples carry a significant amount of vibration signal because the induced vibration quickly dissipates in time, and because the period between two vibration pulses, or "push pulses," is too long. Moreover, the duty cycle of the push pulse is very low and only a few motion detection samples will have significant displacement present. Another exemplary drawback with this method is that the desired harmonics are determined by the period of the pulse sequence; thus, the period must be long enough to produce harmonics in the hundreds of Hz. On the other hand, a significant number of samples must be acquired within one period to satisfy the Shannon sampling theorem and to meet the Nyquist criterion. For example, if the push pulse repetition frequency, $f_p$, is 156.25 Hz and eight harmonics are desired, the pulse repetition frequency ("PRF") of the pulse-echo measurements for the motion tracking has to be 2.5 kHz or higher. In this example, 16 detection pulses are transmitted between two consecutive push pulses; however, because the tissue vibration quickly damps over time, once the excitation pulse is complete only the first few detection pulses will carry meaningful information about the vibration.

There is a significant amount of interference in isolating the motion at a specific frequency. The vibration induced by the periodic pulses includes the fundamental repetition frequency, $f_p$, and its entire harmonics. The decrease of the force amplitude of the higher harmonics can be relatively slow as the frequency increases. In the motion estimation process, the other frequency components interfere with the estimation of the selected frequency component. This interference also includes artifacts that can occur from aliasing of the sampled signal where frequency components above one-half the PRF can overlap into the frequency range of interest.

Weak vibrations at higher harmonics may cause unreliable estimations for tissue shear viscoelasticity. The amplitude of the force at the $n^{th}$ harmonic frequency is proportional to:

$$\text{sinc}(T_b \cdot n \cdot f_p) \quad \text{Eqn. (1);}$$

where $\text{sinc}(x)=\sin(\pi x)/\pi x$ is the so-called cardinal sine function. Thus, the amplitude of the higher frequency components of the acoustic force is significantly smaller than for the lower frequency components. In addition, the tissue tends to substantially attenuate the high frequency vibrations. These factors can make it difficult to measure the shear wave speed components at higher frequencies.

It would therefore be desirable to provide a method for shearwave dispersion ultrasound vibrometry ("SDUV") that produces vibratory motion in a manner such that it can be sufficiently measured before it dissipates in time, produces vibratory motion that does not produce significant interference during measurements, and produces vibratory motion that can be tailored such that the power of higher frequency components can be independently adjusted to offset attenuative losses.

SUMMARY OF THE INVENTION

The present invention overcomes the aforementioned drawbacks by providing a method for shear wave dispersion ultrasound vibrometry ("SDUV") in which vibratory motion is produced in a subject by directing an ultrasound transducer with an excitation signal that is composed of orthogonal basis functions each having a given frequency component or set of frequency components. Such a method produces vibratory motion that does not dissipate quickly in time. In addition, because the frequency components are orthogonal to each other, they do not produce significant interference during measurements. Furthermore, because the excitation signal is composed of multiple orthogonal basis functions, the power of these orthogonal basis functions can be independently adjusted such that higher power levels are attributed to higher frequency components such that attenuative losses at higher frequencies are mitigated.

It is an aspect of the invention to provide a method for producing vibratory motion in the form of a shear wave in a tissue of interest. The shear wave is induced in the tissue using ultrasound energy that is produced by directing an ultrasound transducer with an excitation signal that is composed of orthogonal basis functions, such as sine functions. Each orthogonal basis function has a specified frequency component, of which the power level is adjustable. The frequency component of such an orthogonal basis function is herein referred to as an "orthogonal frequency component," or simply, an "orthogonal frequency." As noted above, the frequency component may also include a set of frequency components. Wave speeds are calculated at each of the orthogonal frequencies present in the induced shear wave, and from which estimates of tissue mechanical properties such as shear elasticity and viscosity are produced.

It is another aspect of the invention to provide a method for SDUV, in which an excitation signal is designed to direct an ultrasound transducer to produce ultrasound energy that induces vibratory motion at several vibration frequencies corresponding to the orthogonal frequencies in the excitation signal. Because the excitation signal is composed of orthogonal basis functions, the power at high frequencies can be increased, interference can be minimized, and efficient interleaving schemes of motion detection and vibration pulses can be provided. The produced ultrasound energy is concentrated in the selected orthogonal frequencies in order to increase the vibration efficiency while minimizing power beyond the desired bandwidth.

It is yet another aspect of the invention to provide a method for performing SDUV, in which the power levels of each orthogonal frequency component in the excitation signal are adjustable such that high power levels can be used for high vibration frequencies.

It is yet another aspect of the invention to provide a method for performing SDUV, in which an efficient interleaving scheme for the vibration and detection using an array transducer is utilized. This interleaving scheme ensures that received detection signals are sampled from strong vibrations before they are attenuated in time, while meeting the Nyquist criterion required to prevent aliasing. Thus, the vibration and measurement time required for characterizing tissue in motion are also reduced.

It is yet another aspect of the invention to provide a method for performing SDUV, in which a pulse-echo ultrasound detection method is used for measuring all of the orthogonal frequency components of the shear wave at several locations. Because the frequencies are orthogonal, each orthogonal frequency of the induced shear wave can be estimated without interference from the other frequencies. Propagation speeds at the orthogonal frequencies are calculated using, for example, Fourier analysis or a fast Fourier transform, or a filter such as a Kalman filter. Shear wave speeds at the orthogonal frequencies are fit to a dispersion model in order to calculate the shear elasticity and viscosity.

It is yet another aspect of the invention to provide a method for performing SDUV, in which the excitation signal includes multiple composed vibration pulses in one period of the fundamental vibration frequency. There are multiple vibration pulses in the one period. The positions, amplitudes, and widths of the pulses are adjusted to maximize the induced vibration for all harmonics. The method increases the vibration information contents in the all detected samples in one period of the fundamental vibration frequency.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
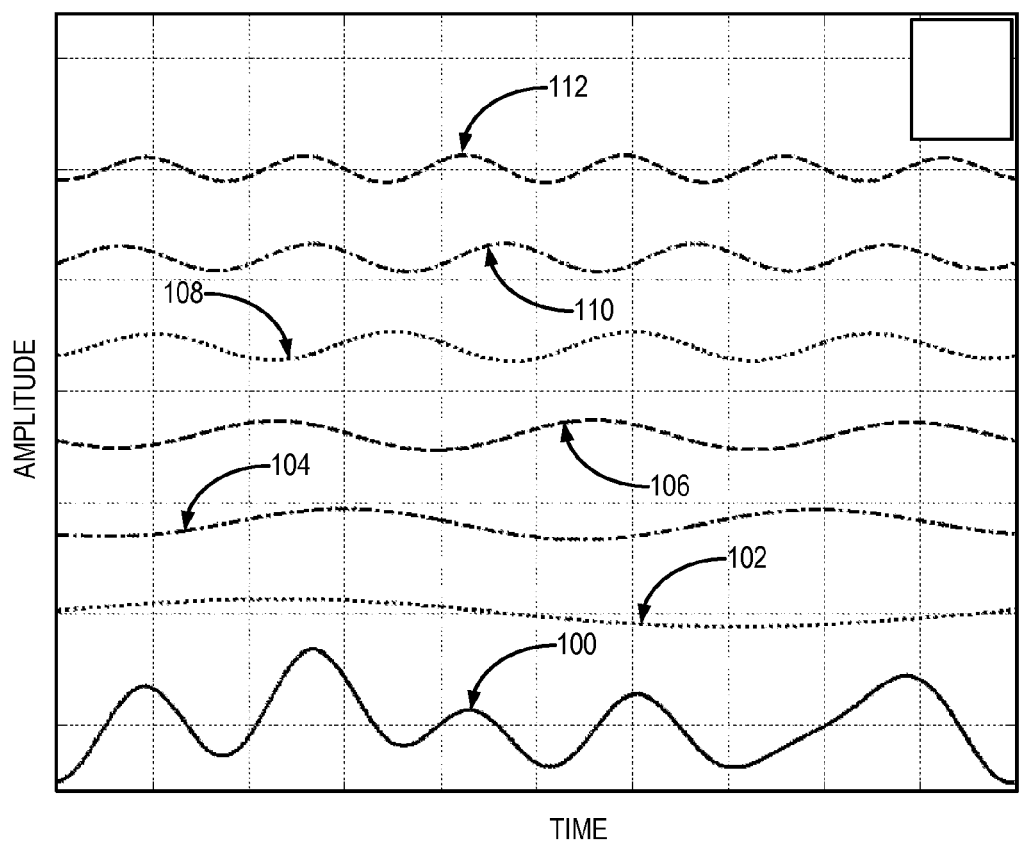
FIG. 1 is an illustrative example of an orthogonal frequency excitation signal and its component basis functions.

In shearwave dispersion ultrasound vibrometry ("SDUV") methods, where a tissue of interest that is buried deeply beneath other tissues, optical methods for measuring the very small harmonic motions imparted to the tissue cannot be used. This problem is solved by employing an ultrasound system, such as an ultrasound imaging system, to interrogate the tissue of interest with a pulsed ultrasound beam and to examine the resulting echo signals in order to measure the phase and amplitude of the harmonic motion imparted to the tissue of interest.

SDUV uses focused ultrasound to generate an acoustic radiation force in a desired tissue region. The radiation force induces vibrations in the tissue as well as a propagating shear wave. The vibratory motion created due to the shear wave propagation is detected using ultrasound-based pulse-echo measurement methods. Intermittent pulses are used to vibrate the tissue and detect the vibration over a distance. By way of example, a set of N tone bursts of length $T_b$ are repeated at a period of $T_p$, which corresponds to a rate, $f_p$, that is equal to $1/T_p$. The pushing pulses produce a radiation force at frequencies of $f_p$ and its harmonics. For example, $f_p$ may be 100 Hz, in which case the shear wave harmonic components will be at 200 Hz, 300 Hz, 400 Hz, and so on. The harmonics in the shear wave spectrum should not be confused with "harmonic imaging" common in medical ultrasound imaging, as those frequencies are in the megahertz range. The speed of the induced shear wave is measured by evaluating the phase shift of the shear wave at a given frequency over a propagation distance according to, $$c_s(\omega) = \frac{\omega \Delta r}{\Delta \phi}; \quad \text{Eqn. (2)}$$

where $\omega$ is the frequency of the shear wave, $\Delta r = r_2 - r_1$ is the distance between motion detection points, and $\Delta \phi = \phi_2 - \phi_1$ is the phase shift of the shear wave. Measurements of shear wave speeds at multiple frequencies are fit to a model in order to calculate the shear elasticity and viscosity. An exemplary model is the so-called Voigt model, which has the following form:

$$c_s = \sqrt{\frac{2(\mu_1^2 + \omega^2 \mu_2^2)}{\rho\left(\mu_1 + \sqrt{\mu_1^2 + \omega^2 \mu_2^2}\right)}}; \quad \text{Eqn. (3)}$$

where $\mu_1$ is the shear elasticity modulus, $\mu_2$ is the shear viscosity, $\omega$ is frequency, and $\rho$ is the density of the tissue.

A method for performing SDUV that utilizes the simultaneous vibration of tissue with several orthogonal frequencies is provided. Such a method is herein referred to as orthogonal frequency ultrasound vibrometry ("OFUV"). In OFUV, vibratory motion in the form of a shear wave is induced in the tissue using ultrasound energy that is produced by directing an ultrasound transducer with an excitation signal that is composed of orthogonal basis functions, such as sine functions. Each orthogonal basis function has a specified frequency component, of which the power level is adjustable. The frequency component of such an orthogonal basis function is herein referred to as an "orthogonal frequency component," or simply, an "orthogonal frequency." The propagation speeds of the shear wave at several orthogonal frequencies are calculated and a quantitative estimation of the tissue shear elasticity and viscosity is performed. The induced vibratory motion has desirable features, including concentrated vibration force at the prescribed orthogonal frequencies; high power in high orthogonal frequencies; minimized interference and sidelobes in the frequency-domain; and high signal powers for detection. In addition, the OFUV method allows for beneficial vibration-detection pulse interleaving schemes and easy implementation.

Tissue is efficiently vibrated by OFUV vibration waves that have a desired spectral distribution that includes several orthogonal frequency components. As noted above, an excitation signal is provided to an ultrasound transducer such that the ultrasound transducer produced ultrasound energy that produces the vibratory motion at the orthogonal frequencies. The excitation signal is formed of several orthogonal basis functions, each having their own frequency component that is orthogonal to the others.

By way of example, the excitation signal is formed by adding several sinusoidal waves, of which the lengths are multiple integers of their periods. Referring to FIG. 1, an exemplary excitation signal 100 and its sine wave components are illustrated. The excitation signal 100 shown in this example is composed of one period of a 100 Hz sinusoidal wave 102, two periods of a 200 Hz sinusoidal wave 104, three periods of a 300 Hz sinusoidal wave 106, four periods of a 400 Hz sinusoidal wave 108, five periods of a 500 Hz sinusoidal wave 110, and six periods of a 600 Hz sinusoidal wave 112. Orthogonality is achieved by ensuring that the length of each sinusoidal signal is a multiple integer of its period. The selection of the orthogonal frequencies is flexible and application specific.

The amplitude of each orthogonal frequency component can be increased as the frequency increases in order to compensate for attenuative losses at higher frequencies. The acoustic radiation force on an object can be defined as, $$F(t) = d_r S \langle E(t) \rangle_T \qquad \text{Eqn. (4);}$$

where F(t) is the radiation force, $d_r$ is the drag coefficient, S is the surface area over which the ultrasound energy acts, and $\langle E(t) \rangle_T$ is the short-term time average of the ultrasound energy density. The short-term time average is computed such that T, the averaging period, is longer than the period of the ultrasound wave, but much shorter than the modulation period, that is, $$\frac{2\pi}{\omega_c} \ll T \ll \frac{2\pi}{\omega_m}; \qquad \text{Eqn. (5)}$$

where $\omega_c$ and $\omega_m$ are the carrier ultrasound frequency and the modulation frequency, respectively. For an absorbing medium, the acoustic radiation force, F(t), can be written as, $$f(t) = \frac{2\alpha \langle I(t) \rangle_T}{c} = \alpha \langle E(t) \rangle_T; \qquad \text{Eqn. (6)}$$

where $\alpha$ is the ultrasound attenuation coefficient and I(t) is the ultrasound intensity. For a propagating plane wave, the energy density is defined as:

$$E(t) = \frac{p^2(t)}{\rho c^2}. \qquad \text{Eqn. (7).}$$

Eqn. (7) is derived from the fact that the acoustic radiation force, F(t) is proportional to $\langle E(t) \rangle_T$, and $\langle E(t) \rangle_T$ is proportional to the square of the pressure amplitude.

Figure 2:
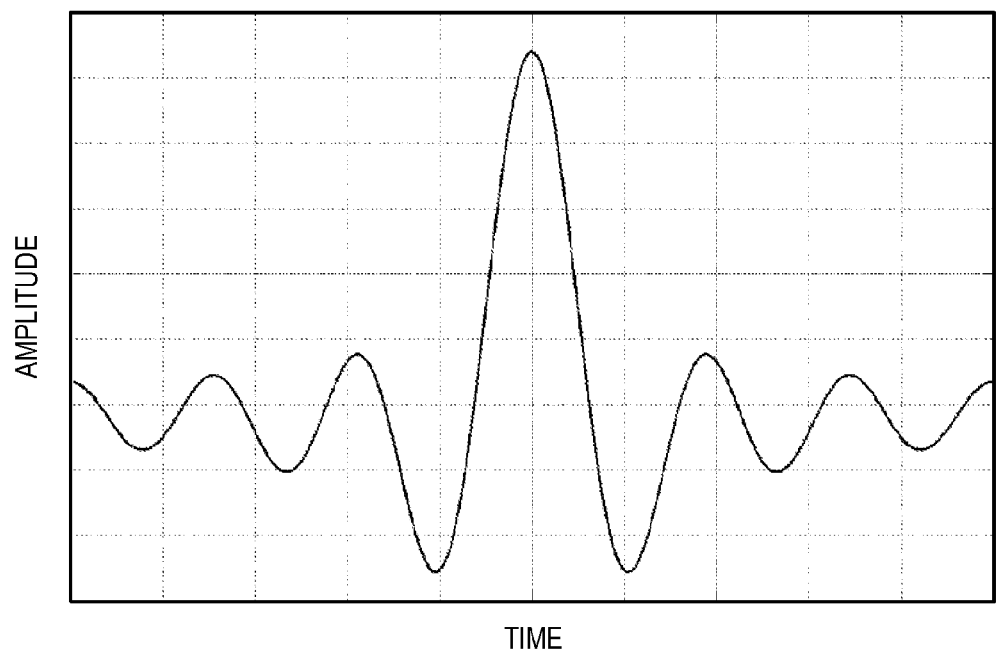
FIG. 2 is an illustrative example of another orthogonal frequency excitation signal formed from the same component basis functions shown in FIG. 1 that have been shifted in phase.

The phase of the orthogonal basis functions that form the excitation signal can be adjusted to obtain different shapes of OFUV waves. For example, in FIG. 1 the phase of the 100 Hz sinusoidal wave 102 is 102 degrees, the phase of the 200 Hz sinusoidal wave 104 is −34 degrees, the phase of the 300 Hz sinusoidal wave 106 is −65 degrees, the phase of the 400 Hz sinusoidal wave 108 is 35 degrees, the phase of the 500 Hz sinusoidal wave 110 is 60 degrees, and the phase of the 600 Hz sinusoidal wave 112 is −20 degrees. However, if the phases of the sinusoidal waves are changed such that the 100 Hz, 300 Hz, and 500 Hz sinusoidal waves (102, 106, and 110) have a phase of 0 degrees, and the 200 Hz, 400 Hz, and 600 Hz sinusoidal waves (104, 108, and 112) have a phase of −180 degrees, then a different excitation signal is formed, as shown in FIG. 2. The two ends of the excitation signal in FIG. 1 are at the minimum, which is desirable to obtain a radio frequency ("RF") signal that starts and ends with small values, thereby minimizing sidelobes in the frequency domain.

Proper windowing in the time-domain will prevent unwanted energy being lost to frequency components that are not of interest, but instead manifest as interference, or sidelobes, in the frequency domain. The exemplary excitation signal shown in FIG. 1 is more consistent in time than the one in FIG. 2, where there is a large pulse in the middle.

The general equation for the OFUV baseband modulation function is:

$$OFUV(t) = \sum_{n=1}^{N} A_n \cdot \cos(2\pi f_n t + \theta_n), \qquad \text{Eqn. (8);}$$

where the length of time, t, is selected so that the length of each sinusoidal signal is a multiple integer of its period; $f_n = n \cdot f_b$ is an integer multiple of a base frequency, $f_b$, which is the lowest orthogonal frequency component; and $A_n$ and $\theta_n$ are the amplitude and phase, respectively, associated with $n^{th}$ orthogonal basis function.

Figure 3:
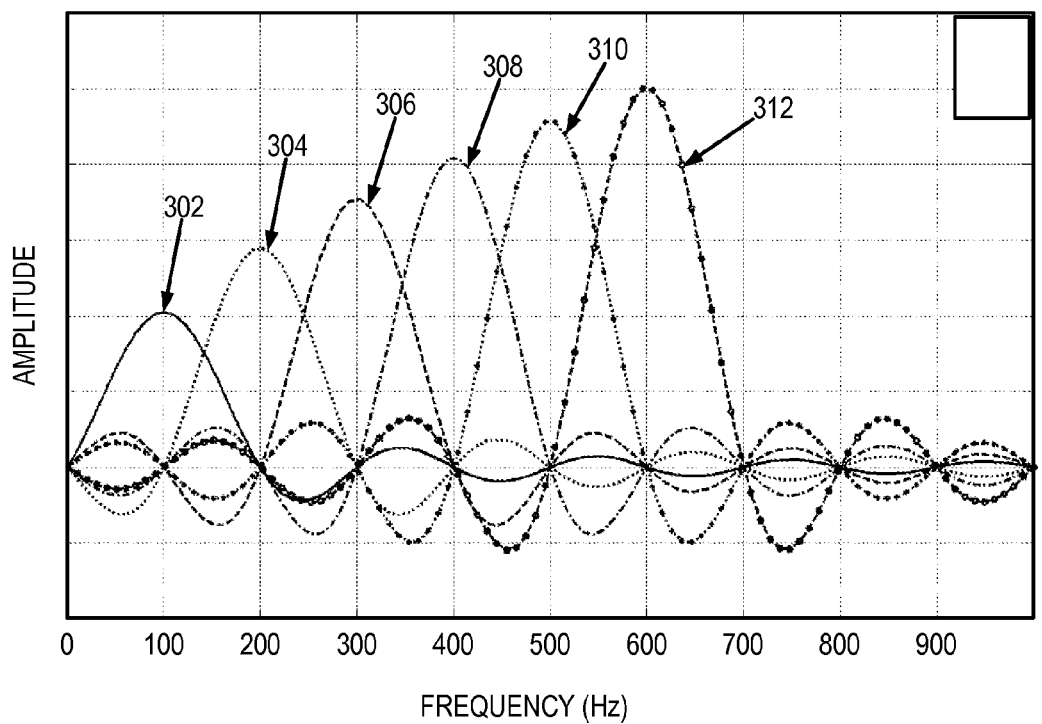
FIG. 3 is a graphic representation of the frequency spectrum of the orthogonal frequency excitation signal shown in FIG. 1.

Since the frequency components of OFUV waves are orthogonal to each other, there is no interference, or stray signal energy, present at the center of any of the orthogonal frequencies. This is shown in FIG. 3 where at the centers of the 100 Hz sinusoidal frequency 302, 200 Hz sinusoidal frequency 304, 300 Hz sinusoidal frequency 306, 400 Hz sinusoidal frequency 308, 500 Hz sinusoidal frequency 310, and 600 Hz sinusoidal frequency 312 interferences from the other frequency components are substantially suppressed.

Figure 4:
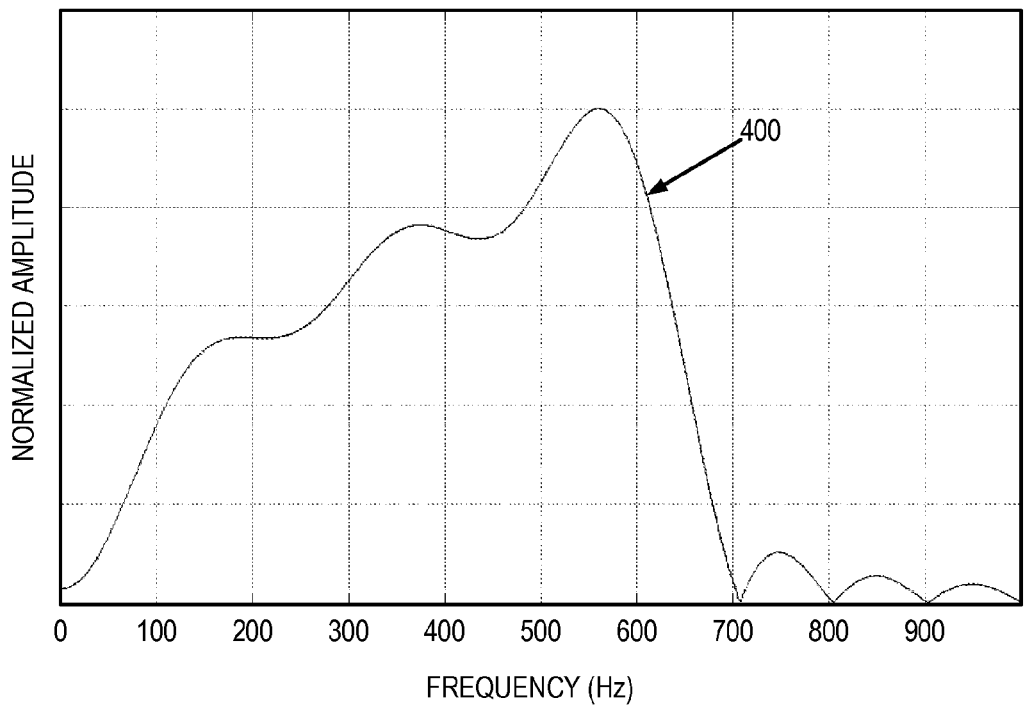
FIG. 4 is a graphic representation of the frequency spectrum of the shortest duration of the orthogonal frequency excitation signal shown in FIG. 2.

When selecting sine waves as the orthogonal basis functions, the excitation signal having the shortest duration has a length that is one period of the lowest frequency in the set of sine waves. In the above example, the shortest length is one period of 100 Hz sinusoidal wave, which is 10 ms, as shown in FIG. 1. The spectral distribution 400 of the shortest excitation signal corresponding to the one shown in FIG. 2 is shown in FIG. 4. Most of the power in the spectral distribution 400 is above DC, or 0 Hz, and below 700 Hz, where the orthogonal frequencies are 100, 200, 300, 400, 500, and 600

Hz. The power at the higher frequencies is higher than those at lower frequencies by increasing $A_n$ as the frequency increases.

Figure 5:
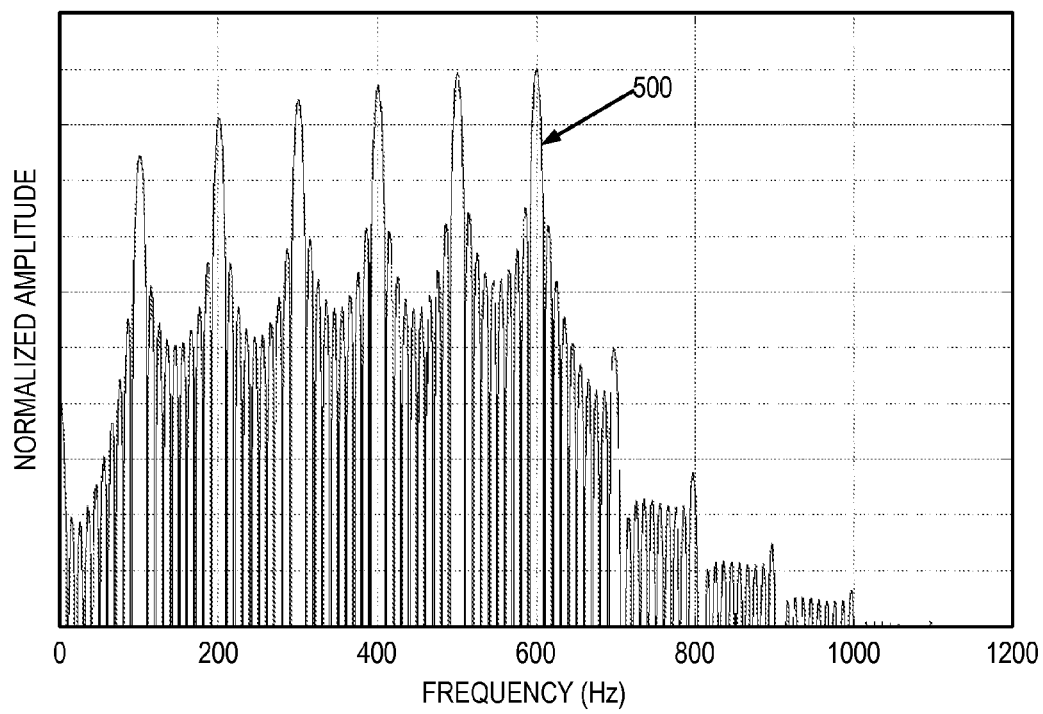
FIG. 5 is a graphic representation of the frequency spectrum of the longest duration of the orthogonal frequency excitation signal shown in FIG. 2.

An excitation signal with a long time duration is used to achieve steady vibration and improved spectral distribution. Based on the above example, if the excitation signal is extended to 100 ms by repeating the signal with the spectrum 400 shown in FIG. 4 ten consecutive times, the spectral distribution 500 shown in FIG. 5 is produced. This orthogonal frequency excitation signal has ten periods of the 100 Hz sinusoidal wave, twenty periods of the 200 Hz sinusoidal wave, thirty periods of the 300 Hz sinusoidal wave, forty periods of the 400 Hz sinusoidal wave, fifty periods of the 500 Hz sinusoidal wave, and sixty periods of the 600 Hz sinusoidal wave. The power of this excitation signal is highly concentrated in the desired orthogonal frequencies, which is efficient for generating tissue vibration and high frequency vibrations having more power. The unwanted sidelobes in the frequency domain are significantly lower than those at the desired orthogonal frequencies.

The excitation signal is obtained by modulating the baseband signal with large-carrier amplitude modulation ("LC-AM") as follows:

$$RF(t) = \sqrt{A_m + OFUV(t)} \cos(\omega_c t) \qquad \text{Eqn. (9);}$$

where $A_m$ is a constant so that the quantity ($A_m$+OFUV(t)) is positive for all times, t; and $\omega_c$ is the carrier frequency, or RF frequency, of the ultrasound transducer. It is important to note that because the force is proportional to the square of the pressure, as shown in Eqns. (4) and (7), the amplitudes of the excitation signals need to be scaled using the square root operator in order to obtain the intended amplitudes in the induced acoustic radiation force. It will be readily appreciated by those skilled in the art that other modulation techniques such as pulse width modulation ("PWM"), pulse amplitude modulation ("PAM"), and pulse position modulation ("PPM") can similarly be utilized to modulate the excitation signal.

Figure 6:
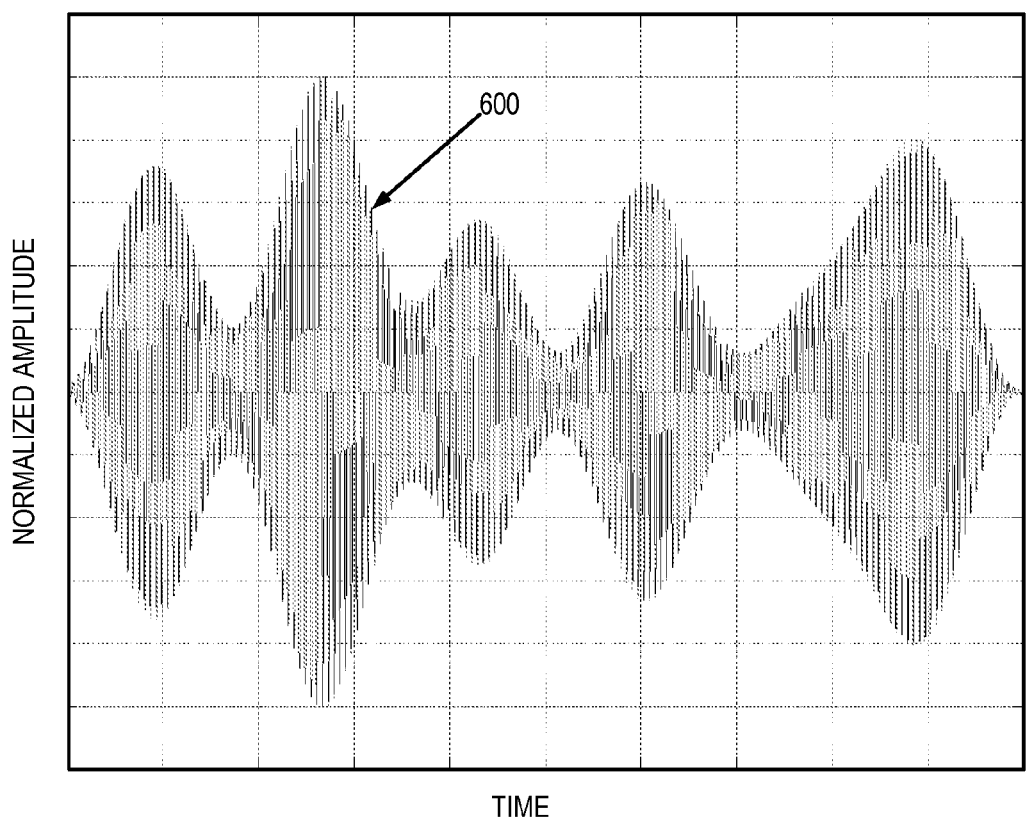
FIG. 6 is a graphic representation of an exemplary orthogonal frequency excitation signal as modulated by a carrier signal.

An exemplary modulated excitation signal 600 is shown in FIG. 6. The two ends of the excitation signal 600 are small in amplitude, which is desirable to minimize unwanted harmonics and sidelobes in the frequency domain. FIG. 6 shows an excitation signal 600 having the minimum length for the selected orthogonal frequencies.

As noted above, the length of the excitation signal can be extended. When the extended length is a multiple integer of the minimum length of the excitation signal, then orthogonality is maintained. In the alternative, an arbitrary length excitation signal can be utilized; however, interference will be introduced at the orthogonal frequencies and the number of sidelobes in the frequency domain may increase.

The foregoing description of an exemplary orthogonal frequency excitation signal was provided with respect to a sinusoidal basis. However, the orthogonal frequency excitation signal can similarly be formed of a generalized set of orthogonal basis functions. Two functions, g(x) and h(x), are said to be orthogonal over the interval [a,b] if their inner product, $\langle g(x), h(x) \rangle$, is zero, where the inner product is defined as, $$\langle g(x), h(x) \rangle = \int_a^b g(x) \cdot h^*(x) dx. \qquad \text{Eqn. (10)}$$

where h*(x) is the complex conjugate of the function h(x). There are many types of basis functions that are orthogonal. Examples of orthogonal basis functions include Bessel functions; spherical harmonic functions; Legendre polynomials; sine and cosine functions; and sets of pulses that do not overlap in time. The result of the modulating function is to obtain a signal that has been designed to have certain characteristics including amplitudes and frequencies. A set of basis functions is used to create a modulating function, or excitation signal, having desired or specified amplitudes at specific frequency components.

For example, a desired frequency spectrum with identified frequency components and their amplitudes can be specified for the radiation force, $F(\omega)$. This signal can be represented in the time-domain as f(t) by performing a Fourier transform on the radiation force, $F(\omega)$.

The OFUV(t) signal in Eqn. (8) is generalized to orthogonal basis ultrasound vibrometry ("OBUV") as, $$OBUV(t) = \sum_{n=1}^{N} A_n \cdot b_n(t); \qquad \text{Eqn. (11)}$$

where $A_n$ is the amplitude of the $n^{th}$ basis function, $b_n(t)$. The set of amplitudes, $A_n$, can be selected as:

$$A_n = \frac{1}{B_n} \cdot \int_0^T f(t) b_n(t) dt; \qquad \text{Eqn. (12)}$$

where T is the duration of the Fourier transform, f(t) of the radiation force, $F(\omega)$, and $B_n$ is a constant given by, $$B_n = \int_0^T b_n(t) b_n(t) dt. \qquad \text{Eqn. (13)}$$

If $b_n(t)$ is orthonormal, $B_n$ is equal to one. Complex conjugation is not used in these integrals because it is assumed that $b_n(t)$ is real. Following this generalization, it can be seen that in Eqn. (8)

$$b_n(t) = \cos(2\pi f_n t + \theta_n) \qquad \text{Eqn. (14).}$$

To form the modulated pressure signal using OBUV(t), then, Eqn. (9) is generalized as, $$RF(t) = \sqrt{A_m + OBUV(t)} \cos(\omega_c t) \qquad \text{Eqn. (15);}$$

where $A_m$ is a constant such that the quantity ($A_m$+OBUV (t)) is positive for all t, and $\omega_c$ is the carrier frequency, or radio frequency, of the ultrasound transducer. Again, the amplitudes of the pressure signals need to be scaled by using the square root operator in order to obtain the desired amplitudes in the forcing function.

The examples provided above are given using cosine functions, or their chopped version described below, as the orthogonal basis functions; however, it will be appreciated by those skilled in the art that many different types of orthogonal basis functions can be readily employed. By way of example, in practice, the basis functions, $b_n(t)$, are determined by the ultrasound system such that they are natural to the apparatus. For example, if an analog transmitter is used, cosine functions could be used to construct an excitation signal. However, typical commercial ultrasound scanners are restricted to transmitting finite amplitude tone bursts, or tone bursts in which amplitudes can change over a limited number of levels, such as 16, for each pulse. In this case, the basis functions are selected as sets of tone bursts where each tone burst in the sequence has an adjustable amplitude, duration, and position in time. With technical advancements, the selection of appropriate basis functions for future ultrasound systems will likely be more flexible and not limited to the examples described in this application. It is noted that the tissue's mechanical response to the applied radiation force serves to act as a low-pass filter and will attenuate undesirable high frequency components that may be generated because of limitations to the basis functions imposed by the ultrasound scanner.

Figure 7:
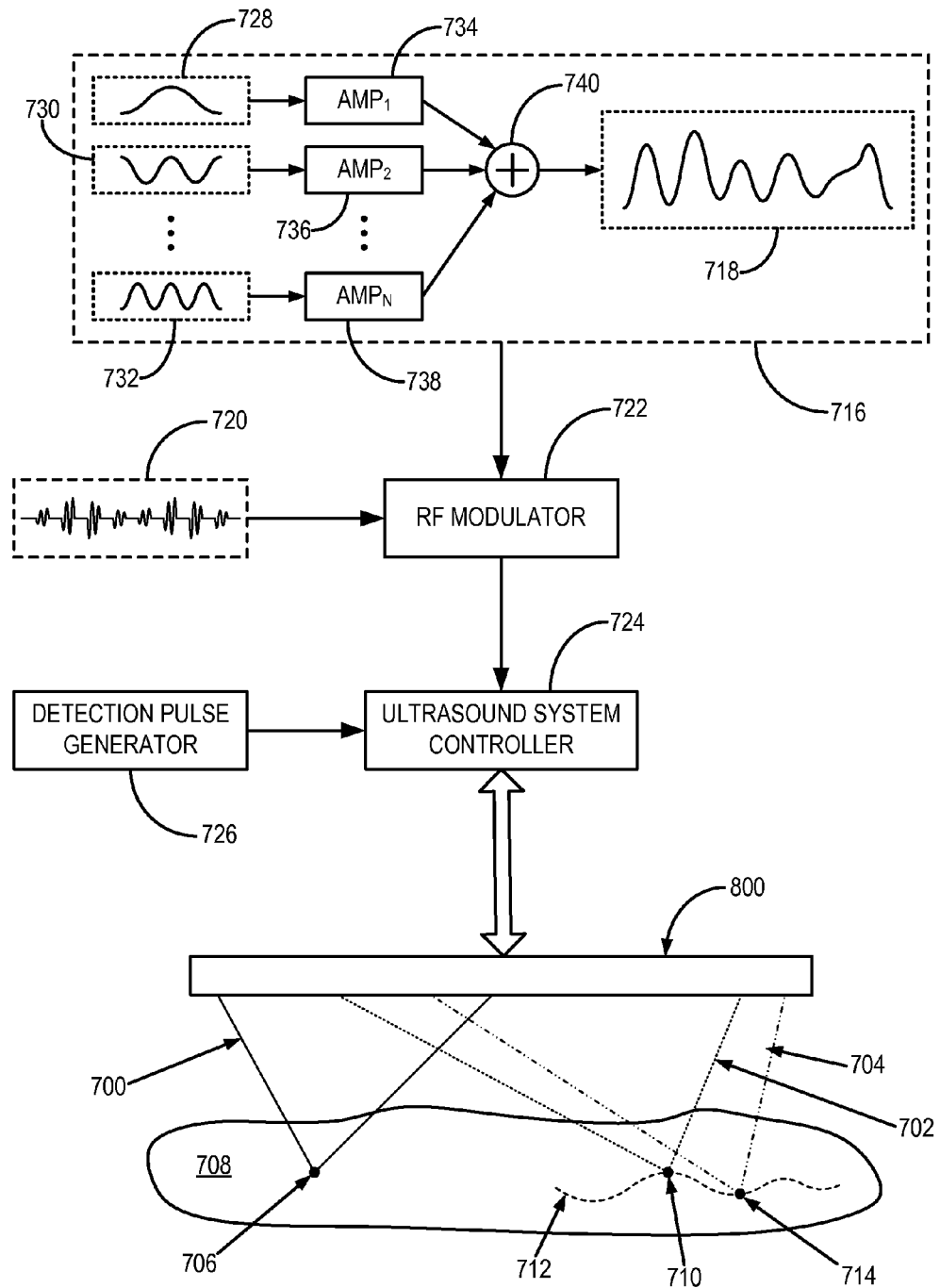
FIG. 7 is a block diagram of an exemplary shear wave dispersion ultrasound vibrometry ("SDUV") system that employs to present invention.

Referring now to FIG. 7, an exemplary SDUV, or OFUV, system that employs the present invention includes an ultrasound transducer 800 that is operable to produce focused ultrasound beams 700, 702, and 704. In particular, the transducer 800, such as a linear array transducer, intermittently transmits a beam of ultrasonic vibration pulses 700 to a vibration origin 706 in the tissue of interest 708 in order to vibrate, or oscillate, the tissue 708 at the prescribed orthogonal frequencies. When the vibration pulses 700 are not being applied to the tissue 708, the focus of the transducer 800 is electronically steered to a motion detection point 710 at a distance, Δr, from the vibration origin 706, and harmonic vibratory motion 712 indicative of an induced shear wave that is occurring at that point is detected. The focus of the transducer 800 can be further electronically steered to a different motion detection point 714, and harmonic vibratory motion 712 detected at that point.

Under the direction of a digital controller of the ultrasound system, which controls the transmission and reception of signals, a vibration mode is multiplexed with a detection mode. This enables the detection of the harmonic motion 712 by the same transducer 800 that transmits the vibration pulses 700. Moreover, in this manner, both vibration and detection can be achieved without mechanically moving the transducer 800.

A signal generator 716 is configured to produce an orthogonal frequency excitation signal 718 in accordance with the present invention. This excitation signal 718 then modulates a signal 720 in an RF modulator 722. The modulated excitation signal is then passed to an ultrasound system controller 724, which is configured to drive the ultrasound transducer 800 in response to the modulated excitation signal. The ultrasound system controller 724 also receives detection pulse signals from a detection pulse generator 726. The detection pulse signals direct the transducer 800 to produce the ultrasonic detection pulses that are directed towards motion detection points, such that ultrasound echoes can be detected therefrom.

The signal generator 716 operates to combine orthogonal basis function signals, such as orthogonal cosine wave functions 728, 730, and 732 in order to form the orthogonal frequency excitation signal 718. As described above, however, exemplary orthogonal basis functions include Bessel functions, spherical harmonic functions, Legendre polynomials, sine waves, cosine waves, and tone burst pulses inherent to the ultrasound system. The amplitudes of the orthogonal basis functions are independently amplified by amplifier circuits 734, 736, and 738 before being combined, for example, by a summing circuit 740.

Figure 8:
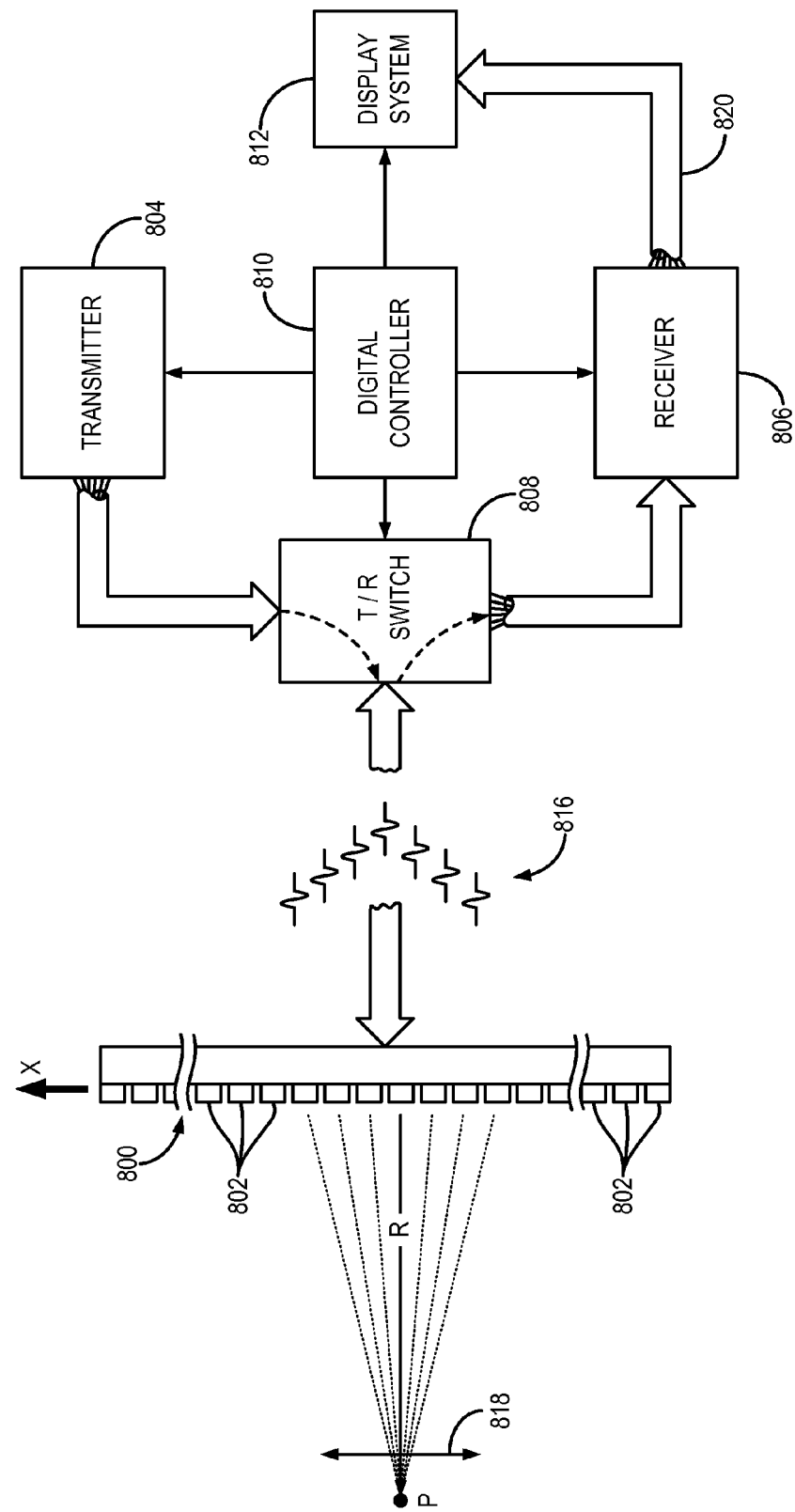
FIG. 8 is a block diagram of an ultrasound system, which forms a part of the SDUV system of FIG. 7.

Referring particularly to FIG. 8, an exemplary ultrasound system, which forms a part of the OFUV system of FIG. 7, includes a transducer array 800 comprised of a plurality of separately driven elements 802 which each produce a burst of ultrasonic energy when energized by a pulse produced by a transmitter 804. The ultrasonic energy reflected back to the transducer array 800 from the subject under study is converted to an electrical signal by each transducer element 802 and applied separately to a receiver 806 through a set of switches 808. The transmitter 804, receiver 806, and the switches 808 are operated under the control of a digital controller 810 responsive to the commands input by the human operator. A complete scan is performed by acquiring a series of echoes in which the switches 808 are set to their transmit position, the transmitter 804 is gated on momentarily to energize each transducer element 802, the switches 808 are then set to their receive position, and the subsequent echo signals produced by each transducer element 802 are applied to the receiver 806. The separate echo signals from each transducer element 802 are combined in the receiver 806 to produce a single echo signal which is employed to produce a line in an image on a display system 812.

The transmitter 804 drives the transducer array 800 such that an ultrasonic beam is produced which is directed substantially perpendicular to its front surface. To focus this beam at a range, R, from the transducer 800 a subgroup of the elements 802 are energized to produce the beam, and the pulsing of the inner elements 802 in this subgroup are delayed relative to the outer elements 802 as shown at 816. A beam focused at point P results from the interference of the small separate wavelets produced by the subgroup elements. The time delays determine the depth of focus, or range R, and this is typically changed during a scan when a two-dimensional image is to be produced. The same time delay pattern is used when receiving the echo signals resulting in dynamic focusing of the echo signals received by the subgroup of elements 802. In this manner a single scan line in the image is formed.

To generate the next scan line, the subgroup of elements to be energized is shifted one element position along the transducer length and another scan line is required. As indicated by the arrow 818, the focal point, P, of the ultrasonic beam is thus shifted along the length of the transducer 800 by repeatedly shifting the location of the energized subgroup of elements 802.

Figure 9:
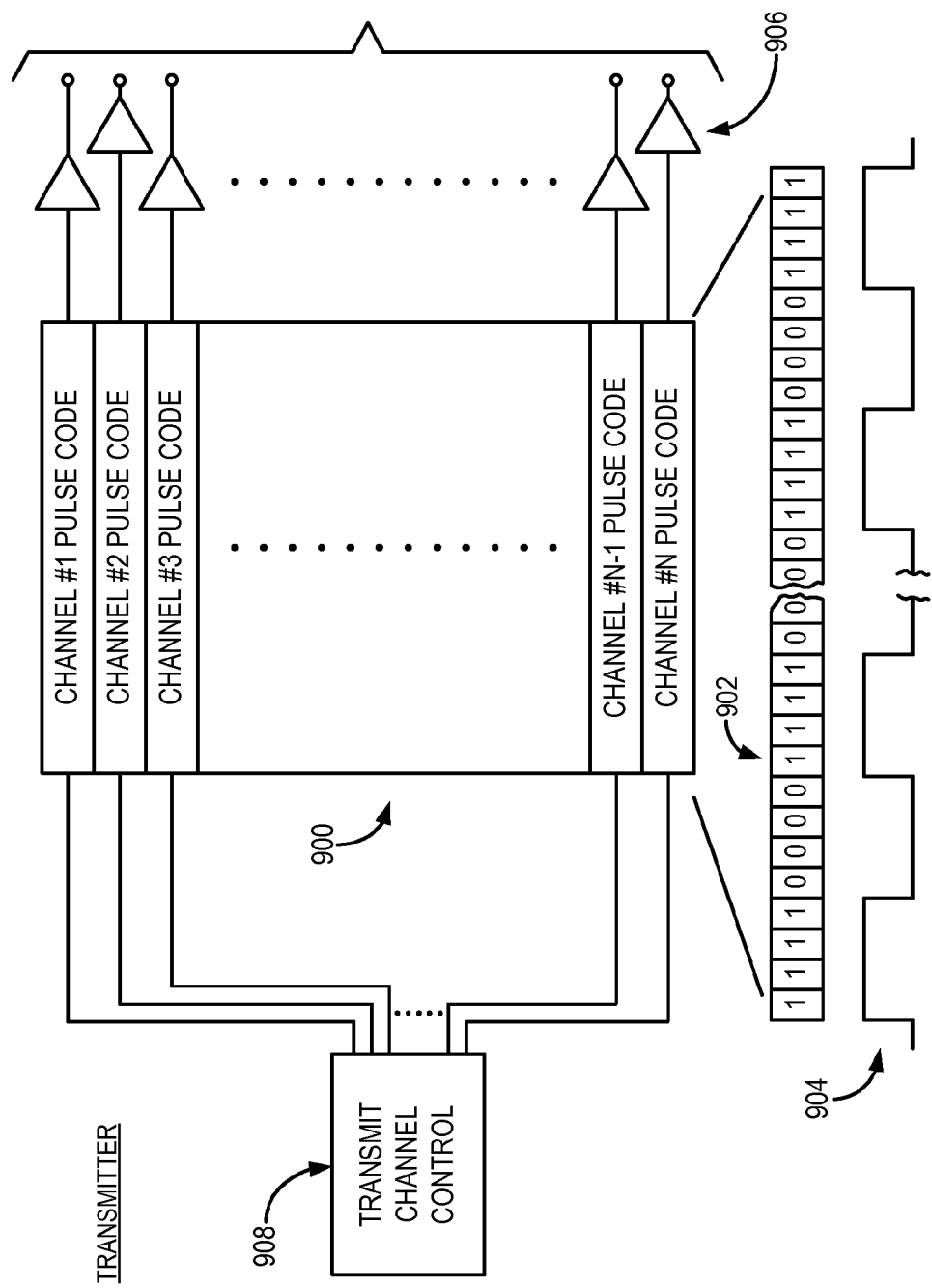
FIG. 9 is a block diagram of a transmitter, which forms a part of the ultrasound system of FIG. 8.

Referring particularly to FIG. 9, the transmitter 804 includes a set of channel pulse code memories which are indicated collectively at 900. Each pulse code memory 900 stores a bit pattern 902 that determines the frequency of the ultrasonic pulse 904 that is to be produced. This bit pattern is read out of each pulse code memory 900 by a master clock and applied to a driver 906 which amplifies the signal to a power level suitable for driving the transducer 800. In the example shown in FIG. 9, the bit pattern is a sequence of four "1" bits alternated with four "0" bits to produce a 5 megahertz ("MHz") ultrasonic pulse 904. The transducer elements 802 to which these ultrasonic pulses 904 are applied respond by producing ultrasonic energy.

As indicated above, to steer the transmitted beam of the ultrasonic energy in the desired manner, the pulses 904 for each of the N channels must be produced and delayed by the proper amount. These delays are provided by a transmit control 908 which receives control signals from the digital controller 810. When the control signal is received, the transmit control 908 gates a clock signal through to the first transmit channel 900. At each successive delay time interval thereafter, the clock signal is gated through to the next channel pulse code memory 900 until all the channels to be energized are producing their ultrasonic pulses 904. Each transmit channel 900 is reset after its entire bit pattern 902 has been transmitted and the transmitter 804 then waits for the next control signal from the digital controller 810. By operating the transmitter 804 in this manner, ultrasonic energy can be focused on a focal point, P, when practicing the herein described method. This focal point can be steered electronically with the appropriate changes to the timing delays provided by the transmit control 908. The term "focal point," as referred to herein, includes not only a single point object in the usual sense, but also a general region-of-interest to which ultrasound energy is delivered in a substantially focused manner.

Figure 10:
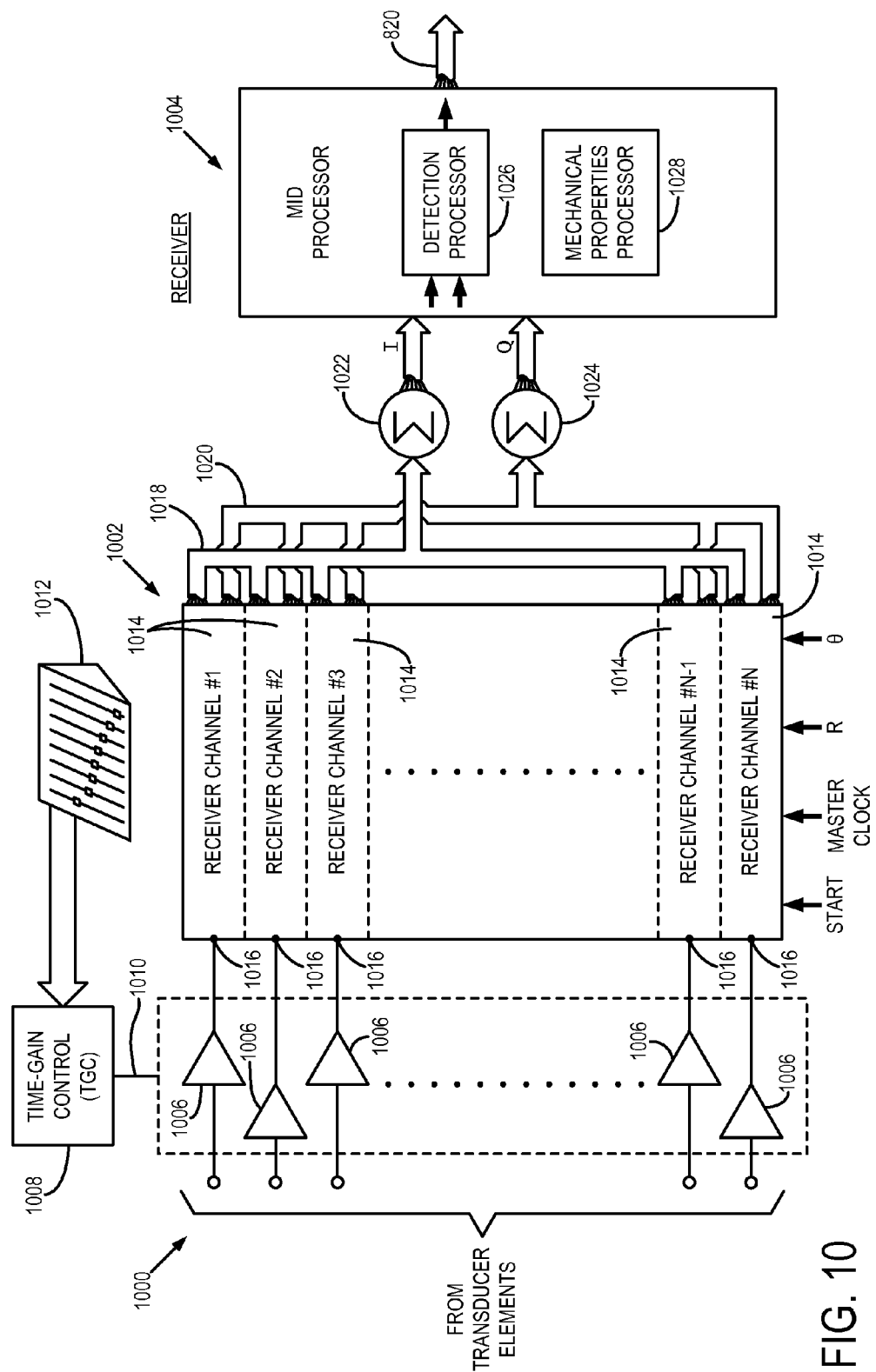
FIG. 10 is a block diagram of a receiver, which forms a part of the ultrasound system of FIG. 8.

Referring particularly to FIG. 10, the receiver 806 is comprised of three sections: a time-gain control ("TGC") section 1000, a beam forming section 1002, and a mid processor 1004. The time-gain control section 1000 includes an amplifier 1006 for each of the N receiver channels and a time-gain control circuit 1008. The input of each amplifier 1006 is connected to a respective one of the transducer elements 802 to receive and amplify the echo signal which it receives. The amount of amplification provided by the amplifiers 1006 is controlled through a control line 1010 that is driven by the time-gain control circuit 1008. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range, R. This amplification is controlled by the operator who manually sets TGC linear potentiometers 1012 to values which provide a relatively uniform brightness over the entire range of the scan. The time interval over which the echo signal is acquired determines the range from which it emanates, and this time interval is divided into segments by the TGC control circuit 1008. The settings of the potentiometers are employed to set the gain of the amplifiers 1006 during each of the respective time intervals so that the echo signal is amplified in ever increasing amounts over the acquisition time interval.

The beam forming section 1002 of the receiver 806 includes N separate receiver channels 1014. Each receiver channel 1014 receives the analog echo signal from one of the TGC amplifiers 1006 at an input 1016, and it produces a stream of digitized output values on an I bus 1018 and a Q bus 1020. Each of these I and Q values represents a sample of the echo signal envelope at a specific range, R. These samples have been delayed in the manner described above such that when they are summed at summing points 1022 and 1024 with the I and Q samples from each of the other receiver channels 1014, they indicate the magnitude and phase of the echo signal reflected from a point, P, located at range, R, on the ultrasonic beam.

Referring still to FIG. 10, the mid processor section 1004 receives the beam samples from the summing points 1022 and 1024. The I and Q values of each beam sample is a digital number which represents the in-phase and quadrature components of the magnitude of the reflected sound from a point, P. The mid processor 1004 can perform a variety of calculations on these beam samples, where choice is determined by the type of image to be reconstructed. For example, if a conventional magnitude image is to be produced, a detection processor indicated at 1026 is implemented in which a digital magnitude, M, is calculated from each beam sample according to:

$$M=\sqrt{I^2+Q^2} \qquad \text{Eqn. (16);}$$

and output at 820 (FIGS. 8 and 10).

The detection processor 1026 may also implement correction methods that, for example, examine the received beam samples and calculate corrective values that can be used in subsequent measurements by the transmitter 804 and receiver 806 to improve beam focusing and steering. Such corrections are necessary, for example, to account for the non-homogeneity of the media through which the sound from each transducer element travels during a scan. The mid processor 1004 also includes a mechanical properties processor 1028 that is configured to calculate the mechanical properties of a tissue of interest in accordance with the present invention.

Details of exemplary methods for calculating such mechanical properties are provided, for example, in co-pending U.S. patent application Ser. No. 10/956,461, which is herein incorporated by reference in its entirety, and in co-pending U.S. patent application Ser. No. 11/536,330, which is herein incorporated by reference in its entirety. In general, however, echo signals are received from one or more motion detection points in the tissue of interest, and these echo signals are processed to detect the harmonic motion at one of the orthogonal frequencies that is indicative of the induced shear wave propagating in the tissue of interest at that same frequency. Thus, a signal representing the harmonic motion at one of the orthogonal frequencies is produced, from which phase values corresponding to the harmonic motion are estimated. Using these phase values, phase difference values are calculated, and from the phase difference values the shear wave speed at the orthogonal frequency is calculated. This process is repeated for each of the orthogonal frequencies and the resultant shear wave speeds are fit to a model, such as the Voigt model, in order to calculate the mechanical properties of the tissue of interest.

The aforementioned orthogonal frequency excitation signal can be implemented in a number of different SDUV configurations. For example, the full orthogonal frequency excitation signal is utilized, with either a single cycle or a set of $N_c$ cycles. This approach utilizes one of two ultrasound system configurations. In the first, two physical transducers are used, one for generating the ultrasonic vibration pulses, and the other used for pulse-echo measurements for motion detection. In the second configuration, the pushing and motion detection pulses are transmitted from a transducer array using different sets of elements and potentially different ultrasound frequencies to minimize interference between signals used for pushing and detection.

Figure 12:
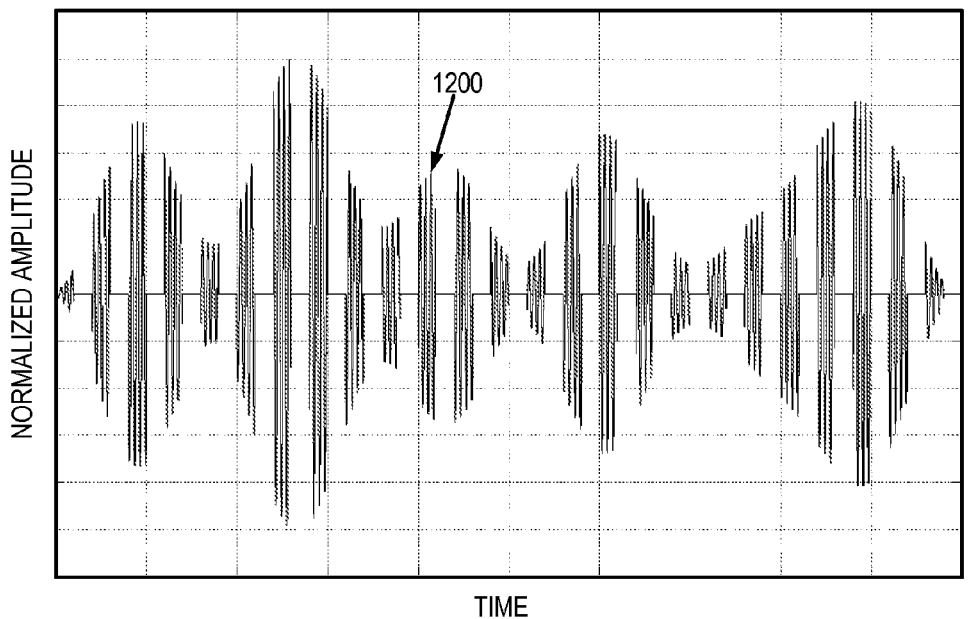
FIG. 12 is an illustrative example of an orthogonal frequency excitation signal that has had selected portions removed.
Figure 13:
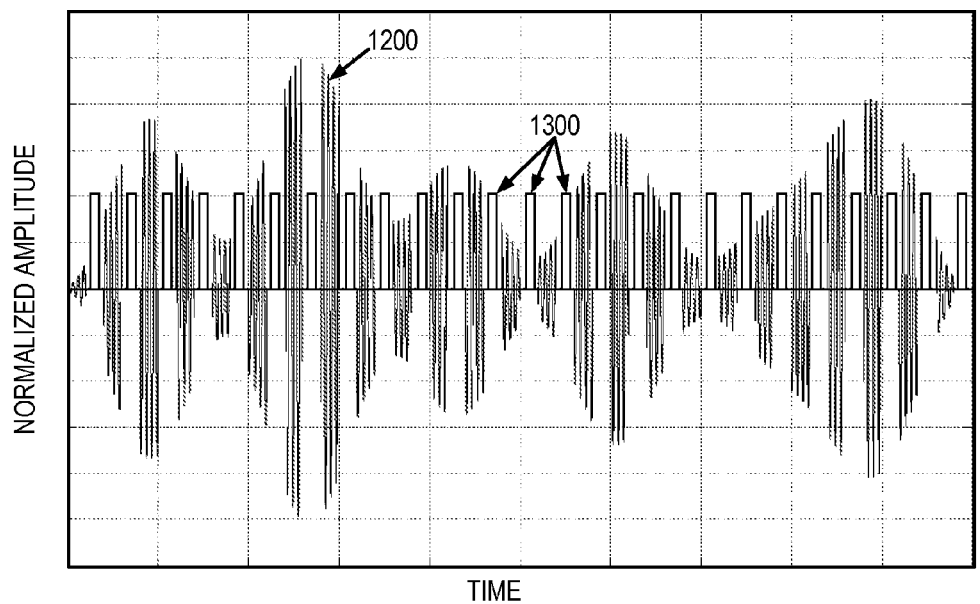
FIG. 13 is an illustrative example of an interleaving time scheme that interleaves the orthogonal frequency excitation signal of FIG. 12 with a series of ultrasonic motion detection pulses directed towards a single motion detection point.

In another configuration, the ultrasonic vibration and detection pulses are interleaved in a time-division scheme. Here, the excitation signal is decimated, or "chopped," such that motion detection pulses can be interleaved with the portions of the excitation signal that are removed during decimation. An example of a chopped excitation signal 1200 is shown in FIG. 12. When the chopped excitation signal is off, detection pulses are transmitted in order to detect the tissue motion over a distance. The detection pulses for different detection locations can be further interleaved to speed up measurement time. The time interval of the interleaved detection pulses for different locations does not have to be the same as the detection pulse repetition period ("PRP") for a given location. An example of the interleaved transmission of a chopped excitation signal and detection pulses is shown in FIG. 13. In this example, $N_d$ detection pulses 1300 are transmitted to M tissue locations (motion detection points) during each off period of the chopped excitation signal 1200 such that the harmonic motion of the induced shear wave can be detected. Thus, the induced tissue shear wave propagation speeds at different orthogonal frequencies can be estimated without moving the ultrasound transducer and without repeating vibration and detection for different locations. For the example illustrated in FIG. 13, the number of motion detection tissue locations is one, M=1, as only one ultrasonic detection pulse is played out during each off period of the excitation signal. For M=2, there would be two different ultrasonic detection pulses played out during each off period, and so on. The pulse repetition frequency ("PRF") of the detection pulses applied to a given motion detection point can be the same as the on-off frequency of the chopped excitation signal. Also, the time interval between two detection pulses transmitted to two different locations can be shorter than that of overall PRP (1/PRF) specified for a single location.

An array transducer can be used to transmit interleaved push and detection pulses. Because the detections at different locations are done at different times, the estimated phase at a given orthogonal frequency needs to be corrected by, $$T_i \omega_n \qquad \text{Eqn. (17);}$$

where $T_i$ is the elapsed time between the transmission of the detection pulses at the first location and at the $i^{th}$ location in a tissue region, and $\omega_n$ is the $n^{th}$ orthogonal frequency. In order to reduce the measurement time and increase the number of detection locations during the off period of the chopped excitation signal, $T_i$ can be selected to be smaller than the detection PRP of a location. In this case, the detection pulses to different locations are substantially immediately transmitted in a consecutive manner without completing the reception of the entire A-scan line for a location.

Regarding the amplitude of the interleaved vibration, or pushing, pulses, the amplitude can be defined in at least two different ways. FIGS. 12 and 13 demonstrate that during the "on" period of the excitation signal, the amplitude of the vibration pulse changes in a continuous fashion. This continuous variation is one of the exemplary manners for defining the amplitude of the vibration pulses. Another way for determining the amplitude assumes a fixed number of discrete voltage levels, $N_l$, available for transmission. If there are $N_l$ levels, the modulation signal varies from 0 to 1, and the voltage amplitude varies from 0 to $V_m$, then the pulse height, A, is rounded to the nearest voltage level such that, $$V = \text{round}\left[A \frac{|V_m|}{N_l}\right] \cdot \frac{V_m}{N_l}; \qquad \text{Eqn. (18)}$$

where round ( . . . ) is a rounding function such as a floor, ceiling, or nearest integer function, or the like, and $|V_m|$ is the unitless magnitude of the voltage amplitude, $V_m$.

Figure 14A:
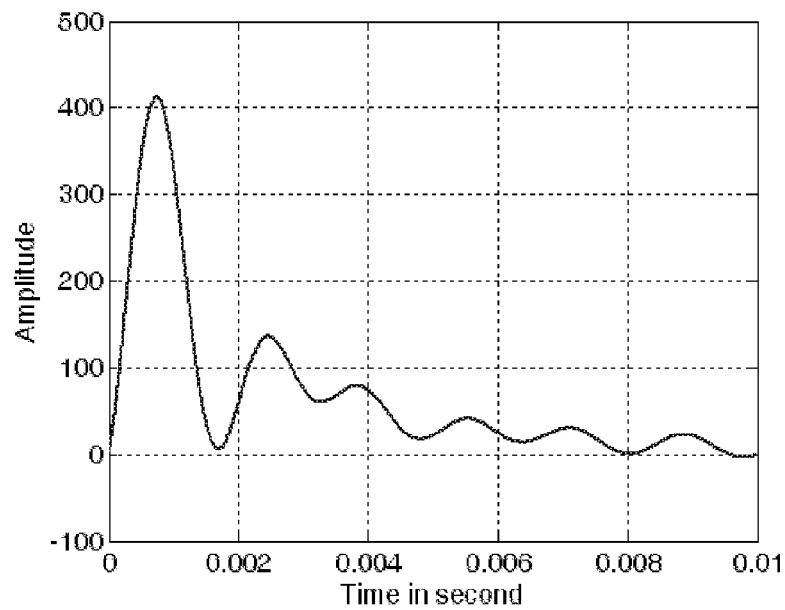
FIG. 14A is an illustrative example of an orthogonal frequency excitation signal that has a centralized location in time that provides a delayed tissue response.
Figure 14B:
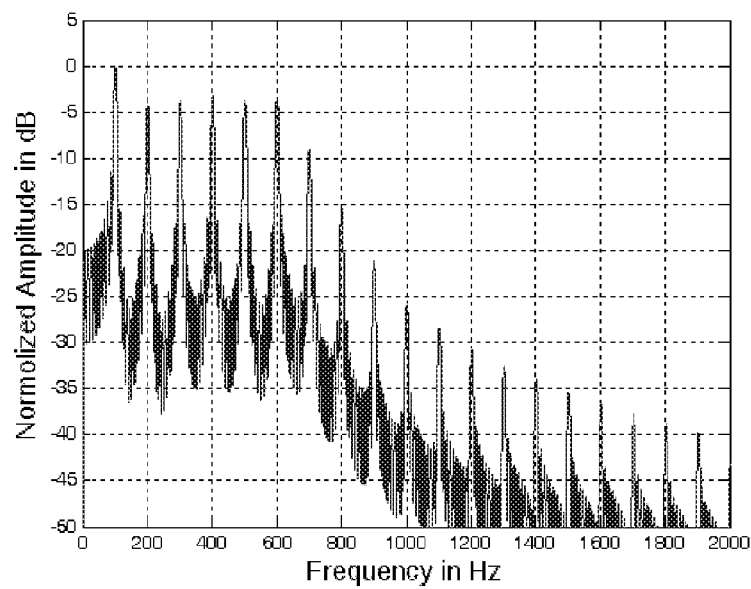
FIG. 14B is a graphic representation of the frequency spectrum of the orthogonal frequency excitation signal of FIG. 14A.

In yet another configuration, a larger dynamic range of tissue displacement is provided by modifying the excitation signal to have a centralized power in time. One such example of this approach is illustrated in FIGS. 14A and 14B. The excitation signal shown in FIG. 14A has a centralized location in time to allow the delayed response of tissue. As a result, the power of the frequency components, as shown in the spectrum in FIG. 14B, is highly concentrated in the desired frequency range, for example, using the orthogonal frequencies described above, in the range of 100-600 Hz.

Figure 15A:
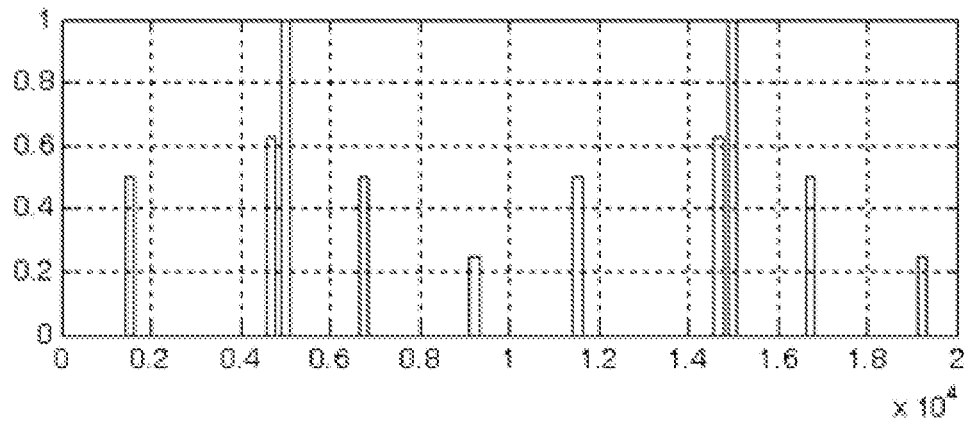
FIG. 15A is an illustrative example of a series of composed vibration pulses utilized to produce vibratory motion in a subject.
Figure 15B:
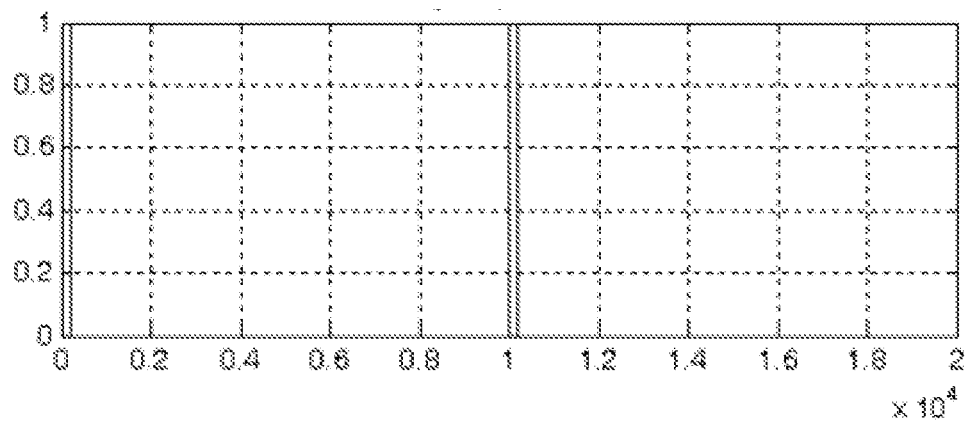
FIG. 15B is an illustrative example of a series of ultrasonic vibration pulses employed with traditional SDUV methods.

In another configuration, the excitation signal is composed of sparsely sampled orthogonal pulses, in which the amplitudes of the orthogonal pulses are derived from the designed modulation signal. With this approach, the performance of the SDUV method is improved by extending the vibration in time and enhancing the higher harmonics of vibrations using multiple vibration pulses in one period of the lowest orthogonal frequency component in the excitation signal frequency band. Such an approach is referred to generally as using "composed vibration pulses." The composed vibration pulses can be distributed to maximize the efficiency of the power delivered in accordance with the present invention. FIG. 15A illustrates an exemplary set of composed vibration pulses over two periods, while FIG. 15B illustrates an exemplary set of vibration pulses typical of previous SDUV methods, also over two periods. In the example illustrated in FIG. 15A, the composed vibration pulses include five sparsely sampled orthogonal pulses in one period of the fundamental frequency. In contrast, the exemplary earlier SDUV approach illustrated in FIG. 15B includes one vibration pulse per period. The composed vibration pulses add vibration power by using additional vibration pulses between two vibration pulses separated by the period, $T_p$. It is contemplated that the composed pulses improve the vibration efficiency because they originate from the orthogonal frequency vibration method.

Figure 15C:
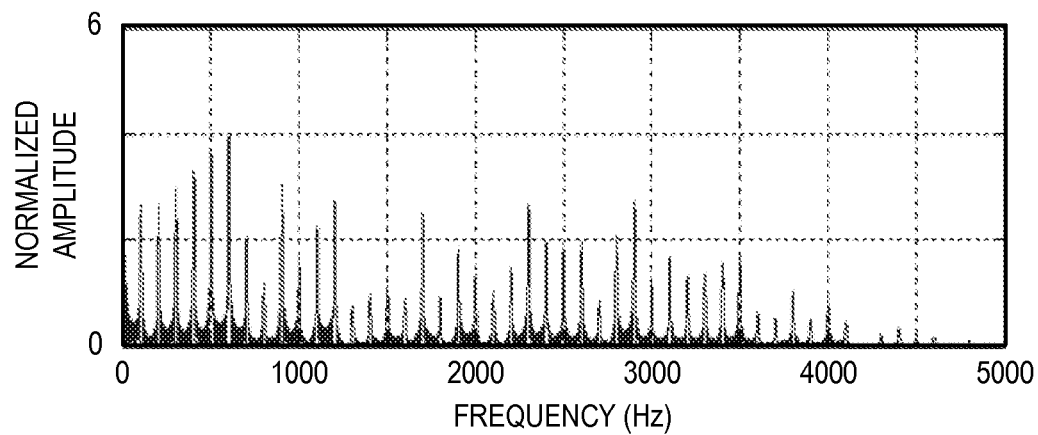
FIG. 15C is a graphic representation of the frequency spectrum of the composed vibration pulses of FIG. 15A.
Figure 15D:
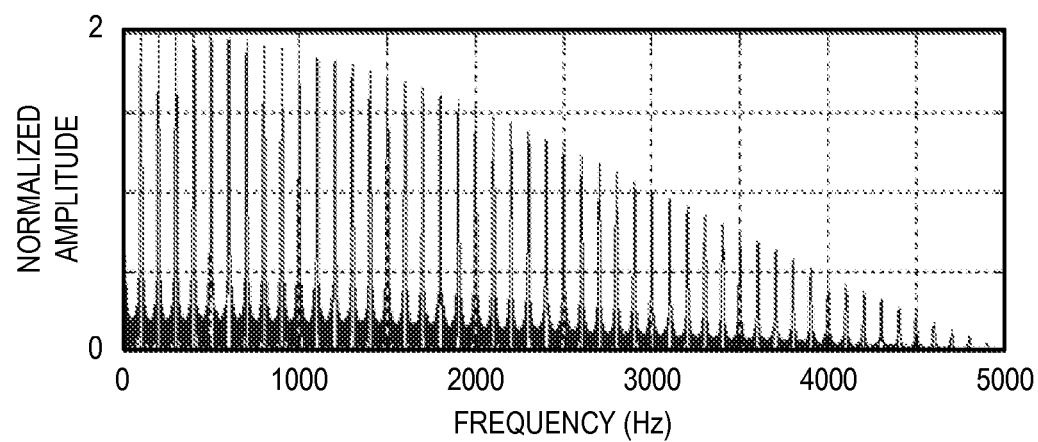
FIG. 15D is a graphic representation of the frequency spectrum of the ultrasonic vibration pulses of FIG. 15B.

FIGS. 15C and 15D illustrate the spectral distributions of the excitation pulses shown in FIGS. 15A and 15B, respectively. The amplitudes of the desired vibration frequencies (e.g., 100, 200, 300, 400, 500, 600 Hz) of the composed pulses shown in FIG. 15C are higher than those of the SDUV pulses shown in FIG. 15D. The vibration increases as the frequency increases in FIG. 15C. In this example, the power of the desired harmonics for the SDUV pulses in FIG. 15D is 23.7 percent of the total power, while the composed pulses have about 36.8 percent in the desired harmonics. This 55 percent improvement in percentage of power in the desired harmonic frequencies holds when both methods transmit the same average power.

In the preceding example, if peak powers are kept the same for both methods, the composed pulses increase the vibration by around 150 percent in the desired frequency range. Note that the vibrations beyond 600 Hz quickly decrease in FIG. 15C, compared with the slow decreases in FIG. 15D. It is a good feature to reduce the aliasing for a limited PRF of the detection pulses. The number of the composed pulses in one period can be from 2 to N, depending on the vibration performance. The positions, amplitudes, widths, and number of the pulses in the composed pulses can be different, as long as the induced vibrations at interested harmonics are increased. For example, the width of the vibration pulses in one period may not be the same and the position may not be fixed. While the orthogonal frequency vibration method guides the design of the composed pulses, the adjustment of pulse parameters should be considered for an optimized performance.

Figure 11:
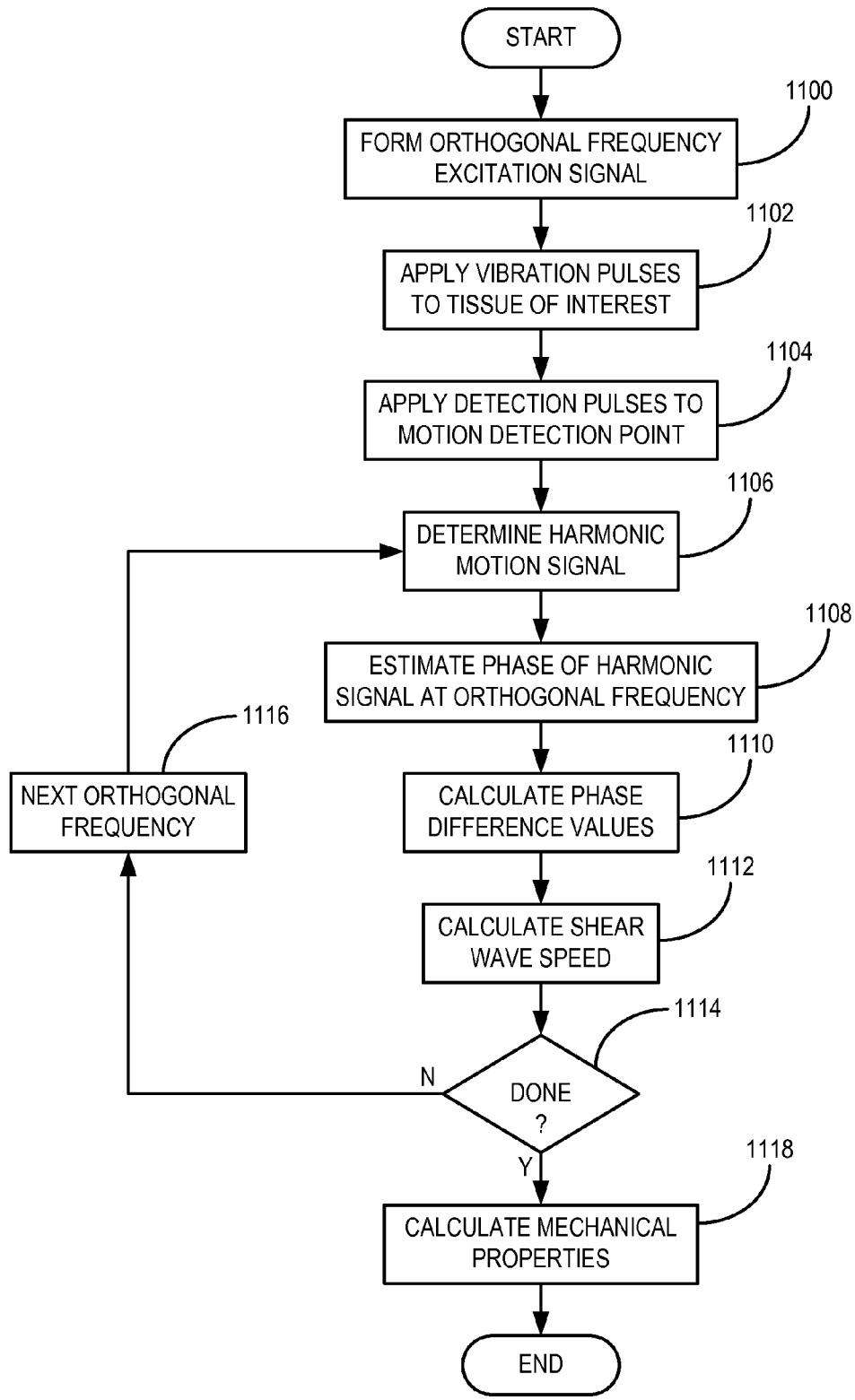
FIG. 11 is a flowchart setting forth the steps of an exemplary method for orthogonal frequency ultrasound vibrometry ("OFUV") in accordance with the present invention.

Referring now to FIG. 11, a flowchart setting forth the steps of an exemplary method for performing OFUV in accordance with the present invention is illustrated. The method begins by forming the orthogonal frequency excitation signal that is utilized to drive the ultrasound transducer, as indicated at step 1100. The excitation signal is produced in any one of a number of different manners, for example, those described above in detail. In general, however, the orthogonal frequency excitation signal is composed of several orthogonal basis functions, each having a given orthogonal frequency component. The excitation signal is then utilized to drive the ultrasound transducer such that ultrasonic vibration pulses are produced and transmitted to a vibration origin in the tissue of interest, as indicated at step 1102. The ultrasound transducer is further directed to transmit ultrasonic detection pulses to one or more motion detection points in the tissue of interest, as indicated at step 1104. As described above in detail, the vibration and detection pulses can be applied sequentially, in an interleaved manner, or substantially simultaneously, and can be produced from different transducers or the same transducer array.

Following the application of ultrasonic detection pulses to the tissue of interest, echo signals are received by the ultrasound transducer. From these received echo signals, a signal indicative of the harmonic motion corresponding to a propagating shear wave corresponding to one of the orthogonal frequencies, as induced by the ultrasonic vibration pulse, is determined, as indicated at step 1106. Thus, the harmonic motion signal is determined for one of the orthogonal frequencies in the excitation signal. Details for this process are described, for example, in co-pending PCT Application No.

US2009/044163, which is herein incorporated by reference in its entirety. From the determined harmonic signal, phase values are estimated for each motion detection point, as indicated at step 1108. Using the estimated phase values, phase difference values between the motion detection points are calculated, as indicated at step 1110. Then, using the phase difference values, a shear wave speed is calculated for the given orthogonal frequency, as indicated at step 1112. A determination is then made at decision block 1114 whether a shear wave speed has been calculated for each of the desired orthogonal frequencies. If not, then the next orthogonal frequency is selected at step 1116, and steps 1106-1112 are repeated to calculate a shear wave speed for this next orthogonal frequency. Once a shear wave speed has been calculated for all of the desired orthogonal frequencies, the mechanical properties of the tissue of interest are estimated, as indicated at step 1118. For example, the calculated shear wave speeds are fit to a model such as a Voigt model, from which shear elasticity and viscosity are estimated.

While the analysis of the received echo signals is performed in the mid-processor section 1004 of an ultrasound receiver, it should be apparent that these functions can also be performed in a separate processor or computer workstation.

It will be appreciated by those skilled in the art that the orthogonal frequency excitation signal described herein can be readily implemented in other ultrasound vibrometry methods. For example, mechanical properties of the tissue of interest can be calculated using information pertaining to the amplitude of vibratory motion induced by directing an ultrasound transducer using the orthogonal frequency excitation signal. An exemplary method of this kind is described, for example, in co-pending U.S. patent application Ser. No. 10/821,461, which is herein incorporated by reference in its entirety.

The present invention has been described in terms of one or more preferred embodiments, and it should be appreciated that many equivalents, alternatives, variations, and modifications, aside from those expressly stated, are possible and within the scope of the invention. For example, the harmonic motion imparted by the ultrasonic vibration pulse can be measured at motion detection points that differ from the vibration origin, or that overlap with the vibration origin. In addition, while aspects of the present invention have been described with respect to inducing vibratory motion in a tissue of interest, it will be appreciated by those skilled in the art that the present invention is also readily applicable to induce vibratory motion in other subjects, such as articles of manufacture undergoing non-destructive testing.

The invention claimed is:

1. A ultrasound system for measuring a mechanical property of a subject, the ultrasound system comprising:
    at least one ultrasound transducer configured to apply ultrasonic energy to a subject and to detect echo signals received therefrom;
    a signal generator configured to generate an excitation signal composed of combinations of orthogonal basis functions, each orthogonal basis function having a corresponding frequency component;
    an ultrasound controller coupled to the at least one ultrasound transducer and the signal generator, and configured to:
        direct the at least one ultrasound transducer, using the generated excitation signal, to apply ultrasonic vibration pulses to a vibration origin in the subject in order to impart a vibratory motion thereto, the imparted vibratory motion including each of the corresponding frequency components;
        direct the at least one ultrasound transducer to apply ultrasonic detection pulses to at least one motion detection point, and to detect echo signals therefrom;
    a processor coupled to the at least one ultrasound transducer and configured to:
        receive the detected echo signals from the at least one ultrasound transducer;
        determine, from the received echo signals, a signal indicative of vibratory motion imparted to the subject;
        estimate at least one of a phase value and an amplitude value of the determined signal indicative of vibratory motion; and
        calculate, using the estimated at least one of a phase value and an amplitude value, a mechanical property of the subject.

2. The ultrasound system as recited in claim 1 in which the orthogonal basis functions are cosine functions and the corresponding frequency components are selected such that each corresponding frequency component is a harmonic of a same fundamental frequency.

3. The ultrasound system as recited in claim 2 in which the signal generator is further configured to truncate each of the cosine functions to include only an integer multiple of its period, in which the integer multiple is equal to the order of the harmonic associated with the corresponding frequency component.

4. The ultrasound system as recited in claim 1 in which the orthogonal basis functions are at least one of Bessel functions, spherical harmonic functions, Legendre polynomials, sine waves, cosine waves, pulses, and tone bursts.

5. The ultrasound system as recited in claim 1 in which the signal generator is further configured to select the orthogonal basis functions such that they correspond to tone bursts inherently produced by the ultrasound system.

6. The ultrasound system as recited in claim 1 in which the signal generator is further configured to remove selected portions of the excitation signal, such that the ultrasound transducer will not be directed to produce ultrasonic vibration pulses during the removed portions, and the ultrasound controller is further configured to apply the ultrasonic detection pulses to the at least one motion detection point during the removed portions of the excitation signal.

7. The ultrasound system as recited in claim 1 in which the signal generator is further configured to remove selected portions of the excitation signal, such that the ultrasound transducer will not be directed to produce ultrasonic vibration pulses during the removed portions, and the portions of the excitation signal that are removed therefrom are removed in at least one of regular intervals and irregular intervals.

8. The ultrasound system as recited in claim 1 in which the at least one ultrasound transducer further comprises a first ultrasound transducer configured to apply the ultrasonic vibration pulses to the subject and a second ultrasound transducer configured to apply the ultrasonic detection pulses to the subject and to detect echo signals therefrom.

9. A method for operating an ultrasound system to produce a propagating shear wave in a subject, the steps of the method comprising:
    a) selecting a set of orthogonal basis functions, each orthogonal basis function corresponding to at least one frequency component;
    b) producing an excitation signal by combining the selected set of orthogonal basis functions; and
    c) directing an ultrasound transducer, using the produced excitation signal, to produce ultrasound energy applied at a vibration origin in a subject, such that a shear wave is produced in the subject in response to vibratory motion induced at the vibration origin by the applied ultrasound energy.

10. The method as recited in claim 9 in which step b) includes independently adjusting at least one of an amplitude and phase of each orthogonal basis function before combining the orthogonal basis functions.

11. The method as recited in claim 10 in which the amplitude of each orthogonal basis function is adjusted such that higher frequency components have a higher power.

12. The method as recited in claim 9 in which an envelope of a radio frequency signal of the ultrasound system is modulated by the excitation signal, and is adjusted at least one of continuously and discretely.

13. The method as recited in claim 9 in which step b) further includes modulating a carrier signal with a square root of the excitation signal.

14. The method as recited in claim 9 in which step b) further includes producing a sparse excitation signal by sparsely sampling the produced excitation signal, and step c) includes directing the ultrasound transducer using the produced sparse excitation signal.

15. The method as recited in claim 9 in which step b) further includes producing a chopped excitation signal by removing selected portions of the excitation signal in at least one of regular and irregular intervals, and step c) includes directing the ultrasound transducer using the produced chopped excitation signal.

* * * * *